(12) United States Patent
Scherson et al.

(10) Patent No.: US 8,932,849 B2
(45) Date of Patent: *Jan. 13, 2015

(54) MICROBIAL PRODUCTION OF NITROUS OXIDE COUPLED WITH CHEMICAL REACTION OF GASEOUS NITROUS OXIDE INCLUDING PHOSPHORUS RECOVERY AND NITRITE REDUCTION TO NITROUS OXIDE

(75) Inventors: Yaniv D. Scherson, Stanford, CA (US); Brian J. Cantwell, Palo Alto, CA (US); Craig S. Criddle, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/586,398

(22) Filed: Aug. 15, 2012

(65) Prior Publication Data

US 2012/0309071 A1 Dec. 6, 2012

Related U.S. Application Data

(63) Continuation-in-part of application No. 13/066,911, filed on Apr. 24, 2011, which is a continuation-in-part of application No. 12/799,677, filed on Apr. 28, 2010.

(60) Provisional application No. 61/575,125, filed on Aug. 15, 2011.

(51) Int. Cl.

| | |
|---|---|
| *C01B 21/22* | (2006.01) |
| *C01B 21/00* | (2006.01) |
| *C01B 21/02* | (2006.01) |
| *C02F 3/30* | (2006.01) |
| *C01B 13/02* | (2006.01) |
| *C02F 3/34* | (2006.01) |
| *C02F 3/12* | (2006.01) |
| *C02F 101/16* | (2006.01) |
| *C02F 103/06* | (2006.01) |
| *C02F 103/26* | (2006.01) |
| *C02F 103/36* | (2006.01) |

(52) U.S. Cl.
CPC . *C01B 21/02* (2013.01); *C02F 3/30* (2013.01); *C01B 13/0203* (2013.01); *C01B 21/22* (2013.01); *C02F 3/302* (2013.01); *C02F 3/34* (2013.01); *C02F 3/1263* (2013.01); *C02F 2101/16* (2013.01); *C02F 2103/06* (2013.01); *C02F 2103/26* (2013.01); *C02F 2103/365* (2013.01); *C02F 2209/02* (2013.01); *C02F 2209/06* (2013.01); *C02F 2209/34* (2013.01)

USPC ........ 435/266; 435/168; 423/239.1; 423/351; 423/358; 423/400

(58) Field of Classification Search
CPC .... C01B 13/0203; C01B 21/02; C01B 21/22; C03F 3/302; C03F 3/34; C03F 3/1263; C03F 2209/34; C03F 2103/06; C03F 2103/26; C03F 2103/365; C03F 2209/02; C03F 2209/06; C03F 2101/16; C03F 3/30
USPC .......... 435/168, 266; 423/239, 351, 358, 400; 431/8

See application file for complete search history.

(56) References Cited

U.S. PATENT DOCUMENTS

| | | | |
|---|---|---|---|
| 4,042,493 A * | 8/1977 | Matsch et al. | 210/625 |
| 5,820,760 A | 10/1998 | Spector | |
| 5,967,099 A * | 10/1999 | Patrick | 123/1 A |
| 6,383,390 B1 | 5/2002 | Van Loosdrecht et al. | |
| 6,485,646 B1 | 11/2002 | Dijkman et al. | |
| 6,846,471 B2 | 1/2005 | Hotta et al. | |
| 7,211,232 B1 * | 5/2007 | Zuberi | 423/210 |
| 2002/0092290 A1 | 7/2002 | Herdy | |
| 2005/0218074 A1 * | 10/2005 | Pollock | 210/637 |

OTHER PUBLICATIONS

Lashof DA and Ahuja DR (1990). Relative contributions of greenhouse gas emissions to global warming. Nature, v344, p. 529-531.*
Gumaelius L et al. (2001) *Comamonas dinitrificans*sp. nov., an efficient denitrifying bacterium isolated from activated sludge. International Journal of Systematic ad Evolutionary Microbiology, v51, p. 999-1006.*
Zhu G et al. (2008). Biological Removal of Nitrogen from Wastewater. Rev Environ Contam Toxicol, v192, p. 159-195.*
Kristjansson JK and Hollocher TC (1980). First practical assay for soluble nitrous oxide reductase of denitrifying bacteria and a partial kinetic characterization. Journal of Biological Chemistry, v255(2), p. 704-707.*
Bock E et al. (1995). Nitrogen loss caused by denitrifying Nitrosomonas cells using ammonium or hydrogen as electron donors and nitrite as electron acceptor. Archives of Microbiology, v162(1), p. 16-20.*
NACWA (Oct. 1, 2009). "Renewable Energy Recovery Opportunities from Domestic Wastewater," 3 pages.*

(Continued)

*Primary Examiner* — Cherie M Stanfield
*Assistant Examiner* — Sean C Barron

(57) ABSTRACT

A method to produce $N_2O$ from organic nitrogen and/or reactive nitrogen in waste uses a bioreactor coupled to a hardware reactor device in which the $N_2O$ is consumed in a gas phase chemical reaction, e.g., catalytic decomposition to form oxygen and nitrogen gas. Heat from the exothermic reaction may be used to generate power. The $N_2O$ may alternatively be used as an oxidant or co-oxidant in a combustion reaction, e.g., in the combustion of methane.

12 Claims, 16 Drawing Sheets

(56) References Cited

OTHER PUBLICATIONS

WERF (Mar. 2009). "Energy Oppurtunities in Wastewater and Biosolids," 2 pages.*

R. Zeng, Z. Yuan, J. Keller, Enrichment of Denitrifying Glycogen-Accumulating Organisms in Anaerobic/Anoxic Activated Sludge System, Biotechnology and Bioengineering vol. 81, Issue 4, pp. 397-404, Feb. 20, 2003.

S. Schalk-Otte, R. J. Seviour, J. G. Kuenen and M. S. M. Jetten, Nitrous Oxide (N20) Production by *Alcaligenes faecalis* During Feast and Famine Regimes, Wat. Res. vol. 34, No. 7, pp. 2080-2088, 2000, Elsevier Science.

J. T. Moraghan and R. J. Buresh, Chemical Reduction of Nitrite and Nitrous Oxide by Ferrous Iron, Soil Sci. Soc, Am. J., vol. 41, 1977.

J. Sorensen and L. Thorling, Stimulation by lepidocrocite (gamma-FeOOH) of Fe(II)-dependent nitrite reduction, Geochimica et Cosmochimica Acta, vol. 55 (1991), pp. 1289-1294.

C. Hellinga, A. A. J. C. Schellen, J. W. Mulder, M. C. M. van Loosdrecht, J. J. Heijnen, The SHARON Process: An Innovative Method for Nitrogen Removal from Ammonium-Rich Waste Water, Water Science and Technology, vol. 37, Issue 9, 1998, pp. 135-142.

H. C. B. Hansen, O. K. Borggaard, J. Sorensen, Evaluation of the Free Energy of Formation of Fe(ii)-Fe(III) hydroxide-sulphate (green rust) and its reduction of nitrite, Geochimica et Cosmochimica Acta, vol. 58 (1994), No. 12, pp. 2599-2608.

V. A. Samarkin, M. T. Madigan, M. W. Bowles, K. L. Casciotti, J. C. Priscu, C. P. McKay, and S. B. Joye, Abiotic nitrous oxide emission from the hypersaline Don Juan Pond in Antarctica, Nature Geoscience, vol. 3, Apr. 25, 2010.

S. Rakshit, C. J. Matocha, M. S. Coyne, Nitrite Reduction by Siderite, Soil Sci. Soc. Am. J. vol. 72, No. 4, pp. 1070-1077, 2007.

R. L. Meyer, R. J. Zeng, V. Giugliano, L. L. Blackall, Challenges for simultaneous nitrification, denitrification, and phosphorus removal in microbial aggregates: mass transfer limitation and nitrous oxide production, FEMS Microbiology Ecology 52 (2005) 329-338.

R. Lemaire et al., "Identifying causes for N2O accumulation in a lab-scale sequencing batch reactor performing simultaneous nitrification, denitrification and phosphorus removal," Journal of biotechnology, 2006, 122, 62-72.

* cited by examiner

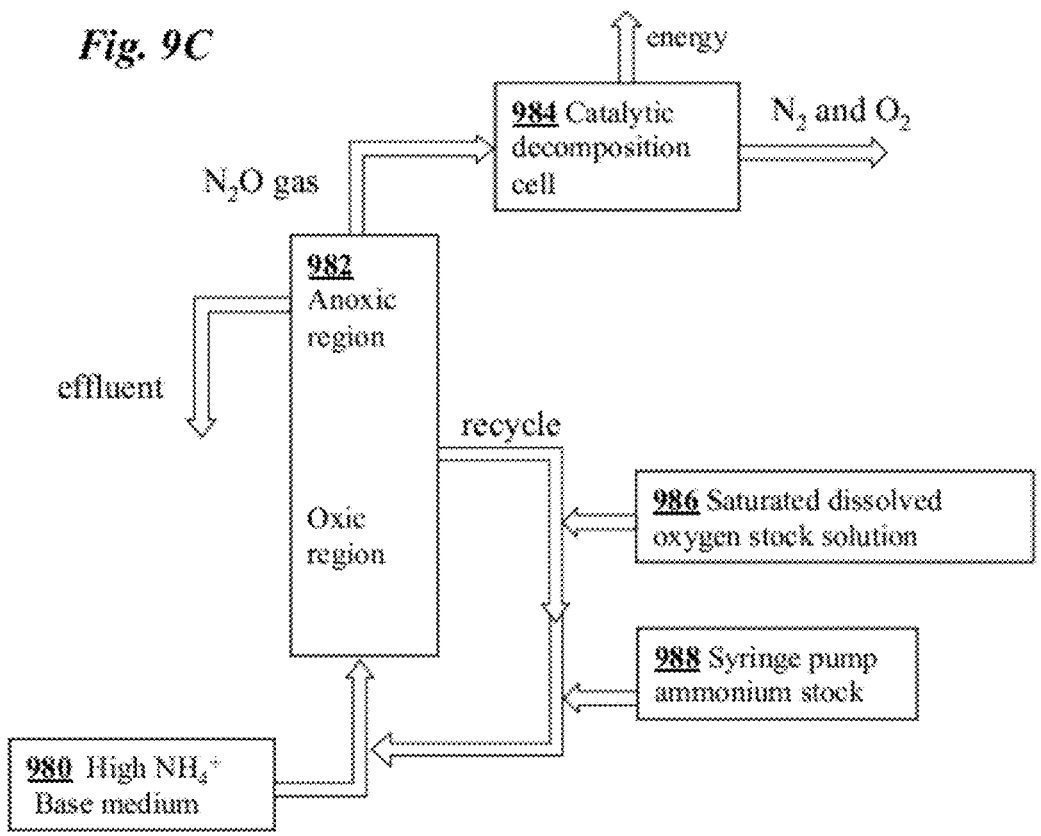

MICROBIAL PRODUCTION OF NITROUS OXIDE COUPLED WITH CHEMICAL REACTION OF GASEOUS NITROUS OXIDE INCLUDING PHOSPHORUS RECOVERY AND NITRITE REDUCTION TO NITROUS OXIDE

CROSS-REFERENCE TO RELATED APPLICATIONS

This application is a continuation-in-part of U.S. patent application Ser. No. 13/066,911 filed Apr. 27, 2011, which is a continuation-in-part of U.S. patent application Ser. No. 12/799,677 filed Apr. 28, 2010, both of which are incorporated herein by reference. This application claims priority from U.S. Provisional Patent Application 61/575,125 filed Aug. 15, 2011, which is incorporated herein by reference.

FIELD OF THE INVENTION

This invention relates generally to devices and methods for removing nitrogen compounds from waste using bioreactors. More specifically, it relates to coupling bioreactors to hardware devices that react nitrous oxide from the bioreactors.

BACKGROUND

With a global warming potential (GWP) 310 times greater than $CO_2$, $N_2O$ is an extremely potent greenhouse gas (GHG). Models of various emission scenarios worldwide published by the IPCC have suggested a steady increase in $N_2O$ production through the 21st century. The impact of such great levels of $N_2O$ would result in a significant increase in atmospheric heat retention.

In addition to $N_2O$, other forms of reactive nitrogen also pose a great threat to the environment. Human alteration of the nitrogen cycle via the Haber process, intensive crop cultivation, and fossil fuel use has approximately doubled the rate of nitrogen input to the terrestrial nitrogen cycle. Loss of this anthropogenic nitrogen to natural systems has led to an array of environmental and public health problems, including ammonia toxicity to aquatic life, eutrophication of nutrient limited natural water bodies, oxygen depletion, and vast dead zones in the ocean margins. It is thus apparent that approaches to $N_2O$ mitigation must be accompanied by strategies to control reactive nitrogen to natural environments.

The traditional objective of wastewater treatment is to achieve complete conversion of nitrogen compounds in waste to $N_2$ gas. This is accomplished by oxidizing the nitrogen to nitrate then reducing the nitrate to $N_2$. $N_2O$ gas is not deliberately produced, but is often incidentally generated at levels that are low but still problematic for greenhouse gas emissions. Due to its negative environmental effects, researchers have never attempted to maximize $N_2O$ production rates. To the contrary, researchers have instead focused on minimizing or eliminating $N_2O$ production in these processes.

Domestic wastewater contains organics and reduced forms of nitrogen (organic N and ammonia) present as soluble and particulate forms and at relatively low concentrations. For the biodegradable organic matter, energy is often recovered as methane using anaerobic consortia of bacteria and archaea. These microorganisms oxidize waste organics, releasing the electrons and hydrogen as methane gas. Bioreactors designed for methane fermentation are common throughout the world, with applications that range in scale from simple low-rate household systems to sophisticated high rate industrial processes. The majority of these anaerobic bioreactors are "digesters", because they have as a major design objective the reduction and stabilization of biomass for disposal.

Bioreactors are also used for nitrogen removal. Their function is to accelerate different steps in the nitrogen cycle, so as to prevent the harmful effects of N discharge: ammonia toxicity to fish, eutrophication, nitrate harm to infants, and dissolved oxygen depletion. In conventional systems, nitrogen is processed as shown in FIG. 3A. Ammonia is oxidized to nitrate, a two-step process termed nitrification that requires 2 moles of $O_2$ per mole of N. This oxygen is added by aeration, a process that constitutes about half of the operating expense of a wastewater treatment plant. The rate-limiting step in nitrification, the oxidation of ammonia to nitrite, is catalyzed by two distinct groups of microbes—the ammonia-oxidizing bacteria (AOB) and the newly discovered ammonia-oxidizing archaea (AOA). Most nitrite is then oxidized to nitrate by several distinct groups of nitrite-oxidizing bacteria (NOB), but under some conditions, particularly under low $O_2$ concentrations, AOB (and possibly AOA) emit $N_2O$ in a nitrite reduction process termed nitrifier-denitrification. Nitrate nitrogen resulting from nitrite oxidation may then be denitrified to $N_2$, a step requiring 5 moles of electrons per mole of N. In conventional systems, the electrons needed for denitrification come from organic matter, decreasing the number of electrons that can be routed to methane production. Denitrification also results in the production of large quantities of waste microbial biomass for disposal.

Over the last decade, innovations in N removal (i.e., the SHARON, OLAND, use of anammox bacteria, CANON processes) have occurred in European labs. These innovations exploit new understanding of microbial ecology so as to "short-circuit" the nitrogen cycle. The result is a significant decrease in the requirements for $O_2$ and reducing power. An example is the CANON process (Completely Autotrophic Nitrification Over Nitrite) illustrated in FIG. 3B. In this process, partial oxidation of ammonium to nitrite by AOB under bioreactor conditions that select against NOB is coupled to the anaerobic oxidation of ammonium to $N_2$ by anammox bacteria. The anammox bacteria convert nitrite and ammonium to $N_2$ gas through a hydrazine intermediate that apparently avoids $N_2O$ production. In principle, this process can achieve a 62% decrease in oxygen and a 90% savings in reducing power, but it is handicapped by the slow growth rates of the anammox bacteria, with doubling times on the order of 10-12 days. Other such innovations can dramatically alter the energy budget for wastewater treatment both by decreasing the energy invested for aeration and increasing the energy recovered as methane. As yet, however, no method of nitrogen removal enables direct energy extraction from the waste nitrogen itself.

SUMMARY OF THE INVENTION

In contrast with conventional wastewater treatment systems designed to avoid or at least minimize $N_2O$ production, embodiments of the present invention couple a bioreactor to a hardware converter device in which the $N_2O$ is consumed in a gas phase chemical reaction. Surprisingly, it is desirable for the bioreactor to have higher, rather than lower, $N_2O$ production. Thus, in one aspect, a method is provided in which a waste stream containing nitrogen compounds is pumped into a bioreactor system and processed to produce nitrous oxide, which is then formed into a gas stream. In a hardware device coupled to the bioreactor system the nitrous oxide gas is then chemically reacted in gas phase, producing energy. For example, the gaseous nitrous oxide may be chemically decomposed to form oxygen and nitrogen gas, or the gaseous nitrous oxide may be an oxidant in a combustion reaction. One of the most striking features of the $N_2O$ decomposition reaction is the fact that the product of the reaction is a mixture of ⅓ oxygen and ⅔ nitrogen—enriched air—plus energy. It is therefore a perfect producer of clean energy.

The bioreactor system may have a single or multiple sequential reaction stages. In some cases, a first stage of the bioreactor system is aerobic (nitrification) and a second stage of the bioreactor system cycles between anaerobic and anoxic stages (partial denitrification). The anaerobic/anoxic stage may involve selection for organisms that generate intracellular storage products (e.g., glycogen, PHA, or PHB) during an anaerobic stage and perform partial denitrifaction to nitrous oxide driven by oxidation of the endogenous carbon during an anoxic stage (i.e., selection for *comamonas* capable of endogenous carbon storage and partial denitrifaction to nitrous oxide).

The processing in the bioreactor system may involve coupled partial denitrification of nitrate or nitrite to nitrous oxide using an inhibitor, e.g., using acetylene ($C_2H_2$) to inhibit nitrous oxide reduction to nitrogen gas ($N_2O$ reductase).

Alternatively, the processing in the bioreactor system of the nitrogen compounds to produce the nitrous oxide may include microbial reduction of nitrite or nitrate to nitrous oxide using organics as an electron donor, e.g., using acetate, volatile fatty acids, or polydroxyalkanoate (PHA) or polyhydroxybuterate (PHB) granules (for example *Commamonas*)

In some embodiments, the processing in the bioreactor system of the nitrogen compounds to produce the nitrous oxide includes microbial reduction of nitrite or nitrate to nitrous oxide using autotrophic organisms capable autotrophic denitrification, e.g., organisms that utilize hydrogen or ammonia as an electron donor during denitrification.

Some embodiments of the invention take advantage of the discovery that a major mechanism by which the organisms produce $N_2O$ is through incorporation and subsequent oxidation of PHB (Polyhydroxybutyrate) within the cell. This provides a mechanism by which organisms may produce high levels of $N_2O$ and provides an avenue for recovery of phosphorus (a major nutrient of value) using techniques of the present invention. Specifically, in such embodiments of the invention the heterotrophic denitrification involves the denitrification to $N_2O$ through incorporation and oxidation of endogenous carbon including PHA.

The method may include processing in the bioreactor system the nitrogen compounds to produce the nitrous oxide by alternating anaerobic and anoxic stages in which phosphate is incorporated into cell biomass in the form poly-phosphate. The method may also include recovering phosphorus from the cell biomass as poly-phosphate.

BRIEF DESCRIPTION OF THE DRAWINGS

FIGS. 9A-C are schematic diagrams illustrating three systems which may be used to implement several embodiments of the invention.

DETAILED DESCRIPTION

General Overview/Flowchart

Figure 1:
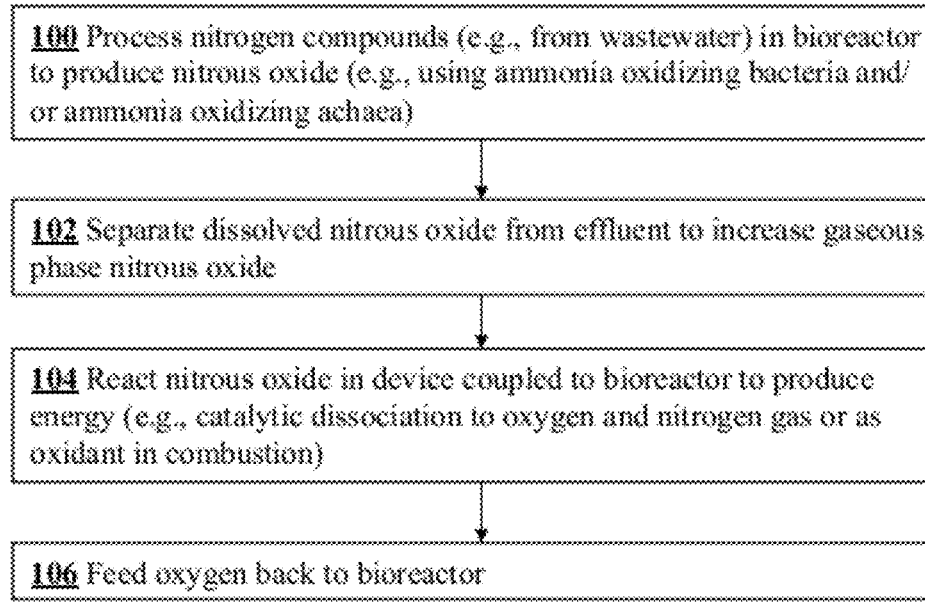
FIG. 1 is a flow diagram illustrating an overview of steps in a preferred embodiment of the invention.

An overview of a preferred embodiment of the invention is shown in the flowchart of FIG. 1. In step 100 nitrogen compounds from waste are processed in a bioreactor system to produce nitrous oxide. Optionally, in step 102 nitrous oxide product dissolved in effluent from the bioreactor is separated to increase the amount of gaseous phase nitrous oxide product. In step 104 the nitrous oxide is chemically reacted in gaseous phase using a hardware device coupled to the bioreactor system. In one configuration, the gaseous nitrous oxide is chemically decomposed to form oxygen and nitrogen gas. In this case, the oxygen may be optionally fed back to the bioreactor in step 106. Alternatively, the gaseous nitrous oxide may be an oxidant in a combustion reaction, in which case no oxygen is fed back.

Figure 2:
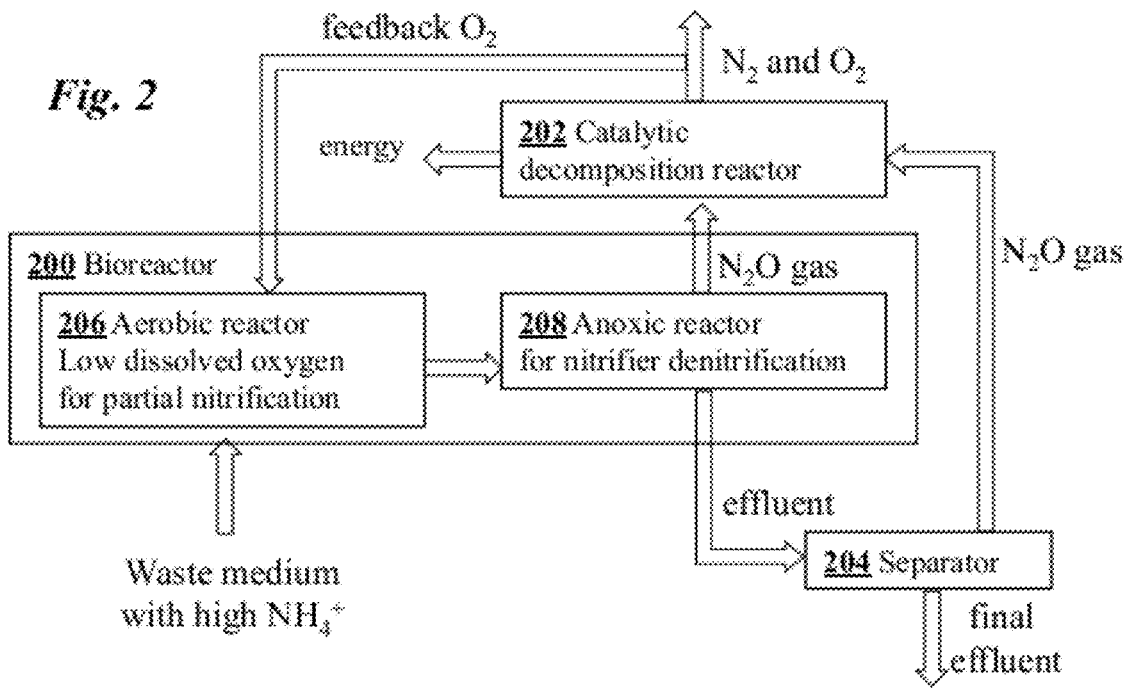
FIG. 2 is a schematic diagram of a coupled bioreactor-catalytic converter system according to one embodiment of the invention.

FIG. 2 is a schematic diagram of a coupled bioreactor-catalytic converter system according to one embodiment of the invention. The system converts waste nitrogen into $N_2O$ for thermal power generation and air for aeration, enabling a low-cost route for removal of soluble and reactive nitrogen species in wastewater, avoiding emissions of the powerful greenhouse gas $N_2O$, and producing oxygen that offsets part of the oxygen demand of waste treatment. The system includes a bioreactor 200 coupled to a catalytic converter device 202. Gas phase $N_2O$ product from the bioreactor 200 is fed to the converter 202. In addition, $N_2O$ dissolved in effluent from the bioreactor is passed through separator 204 to extract dissolved $N_2O$ to produce increased gas phase $N_2O$ which is sent to converter 202. In the converter 202 a catalytic decomposition of the $N_2O$ takes place, producing nitrogen gas and oxygen gas. The oxygen may be fed back to the bioreactor 200 for use in its aerobic stage. In addition, thermal energy from the decomposition reaction in converter 202 may be used for power generation.

Figure 9A:
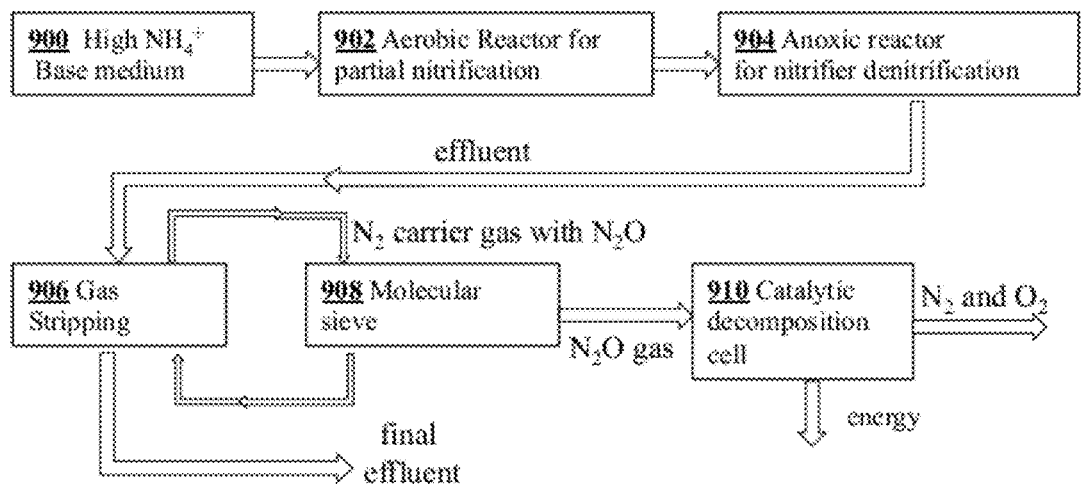
Figure 9B:
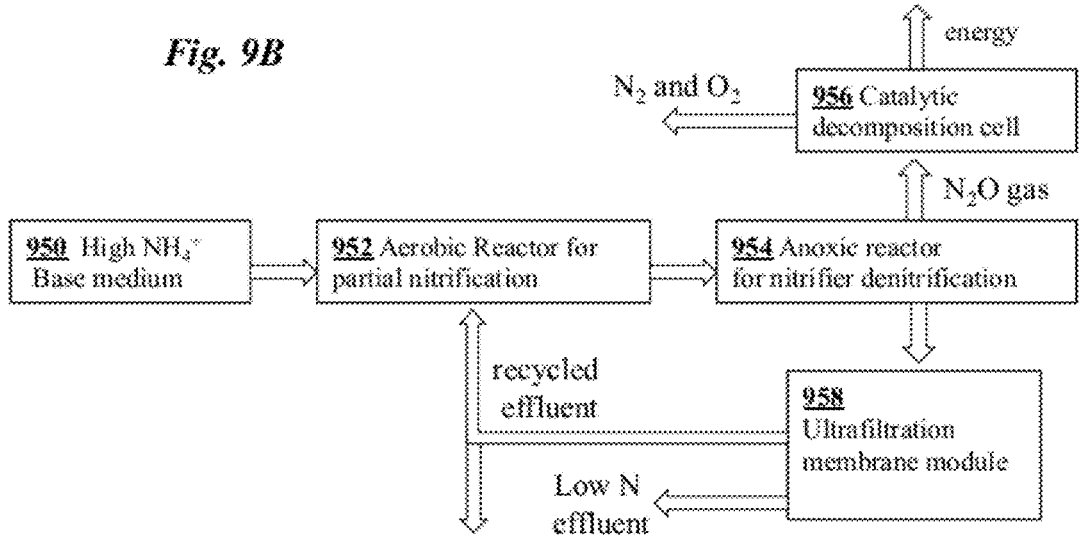

FIGS. 9A-C are schematic diagrams illustrating three different bioreactor-catalytic converter systems according to several embodiments of the invention. As shown in FIG. 9A, a waste stream 900 is pumped into a first aerobic reactor 902 operated with low dissolved oxygen for partial nitrification. The resulting effluent is pumped into a second anoxic reactor 904 for nitrifier denitrification, resulting in an effluent with dissolved $N_2O$. A gas stripper 906 uses $N_2$ carrier gas to remove $N_2O$ from the aqueous effluent. The $N_2$ carrier gas is then passed through a molecular sieve 908 to remove the $N_2O$ in gas phase, and the $N_2$ is recycled back to the gas stripper 906. The $N_2O$ gas is then decomposed in catalytic decomposition cell 910 producing $N_2$, $O_2$, and energy. FIG. 9B shows an embodiment having a waste medium 950 fed through coupled dispersed bioreactors 952 and 954 as in FIG. 9A. $N_2O$ gas from the second reactor 954 is fed to the catalytic decomposition cell 956 producing $N_2$, $O_2$, and energy. The effluent from the second stage reactor 954 passes through an ultrafiltration membrane module 958 to separate the effluent into a low N effluent and a concentrated organism effluent, a portion of which is recycled back to the first stage reactor 952. FIG. 9C shows an embodiment in which waste stream 980 enters attached growth bioreactors forming a reactor 982 with a lower oxic region and a higher anoxic region above which $N_2O$ is collected and then fed to a catalytic decomposition cell 984. A recycling circuit takes effluent from the middle of the reactor 982 between oxic and anoxic regions and recirculates it back to the bottom inlet to the reactor, adding a saturated dissolved oxygen stock solution 986 and ammonium stock 988. The above designs are preferably equipped for temperature and pH control, using synthetic wastewater feed and dissolved oxygen supplied at carefully controlled low levels.

Nitrogen Sources/Applications

The nitrogen compounds entering and processed by the bioreactor may include organic nitrogen and/or reactive nitrogen (e.g., ammonium), such as is commonly found in wastewater, agricultural waste, fertilized agricultural soil, or landfill leachates. The nitrogen compounds may also be derived from biomass production of hydrocarbon fuels, diesel fuel, or ethanol.

Bioreactor Design, Organisms, Stages, and Reactions

In preferred embodiments, the bioreactor system is designed to enhance or maximize the production of nitrous oxide. Bioreactors according to the present invention are different from conventional designs where the focus is always on designing systems that minimize $N_2O$ production and maximize $N_2$ production. In contrast, in embodiments of the present invention the production of $N_2O$ is an end point for nitrifier denitrification or heterotrophic denitrification rather than the production of $N_2$. This is advantageous because, unlike $N_2$, $N_2O$ can be thermally decomposed, releasing $O_2$ and heat.

The processing in the bioreactor system preferably includes nitrification and partial denitrification, or nitrifier denitrification. In one embodiment, the bioreactor is designed for nitrous oxide production by autotrophic nitrification-denitrification of ammonium at low levels of dissolved oxygen. The bioreactor system may have a single or multiple reaction stages. In the embodiment shown in FIG. 2, a first stage 206 of the bioreactor system is aerobic and a second stage 208 of the bioreactor system is anoxic. In various implementations, the second stage of the bioreactor system may be aerated to a dissolved oxygen level below 20% oxygen saturation, or below 3% oxygen saturation, or the second stage of the bioreactor system may be anaerobic.

Figure 3A:
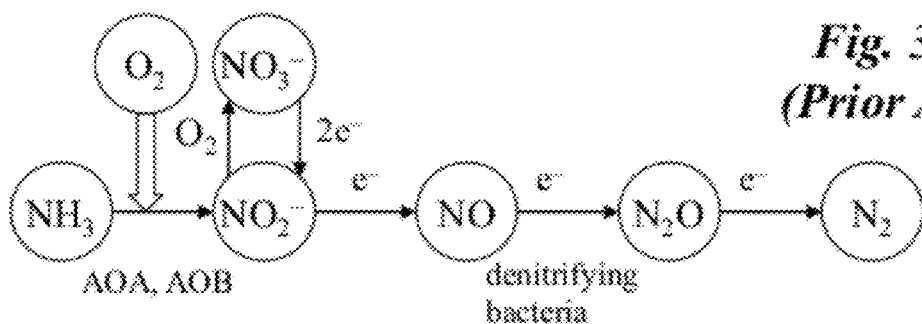
FIG. 3A is a schematic illustration of a conventional technique for microbially processing nitrogen.
Figure 3B:
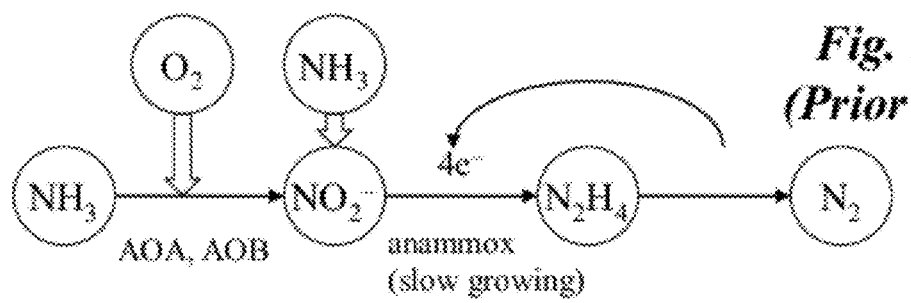
FIG. 3B is a schematic illustration of a more recent known technique for microbially processing nitrogen.
Figure 3C:
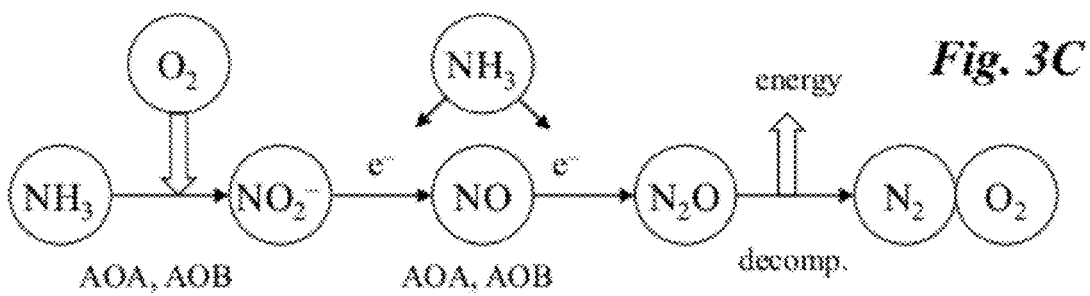
FIG. 3C is a schematic illustration of a technique for microbially processing nitrogen according to an embodiment of the present invention.
Figure 4:
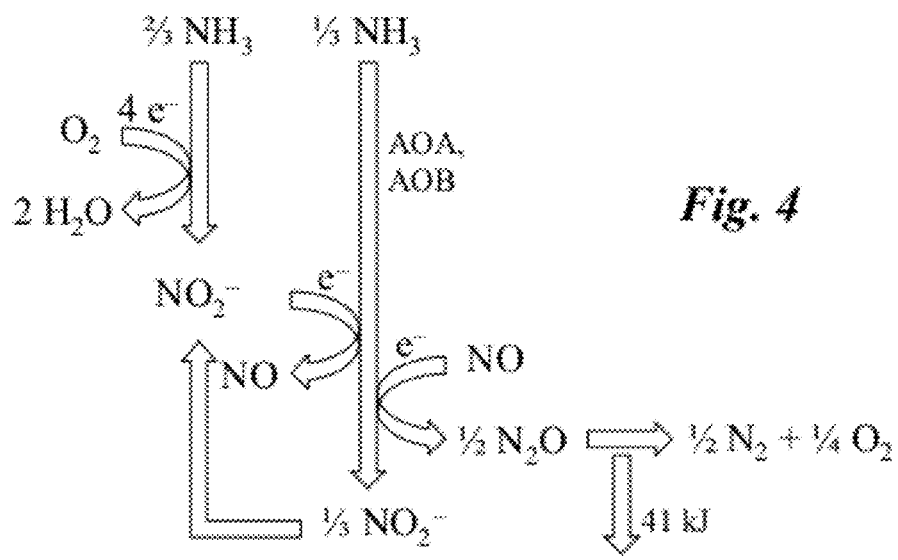
FIG. 4 shows energy reactions and organisms involved in aerobic nitrification-denitrification along with $N_2O$ decomposition according to one embodiment of the invention.

FIG. 4 shows the energy reactions and organisms involved in aerobic nitrification-denitrification along with $N_2O$ decomposition according to one embodiment. These pathways and organisms are preferably exploited in the bioreactor to maximize $N_2O$ production. The process is also shown in FIG. 3C. AOB enrichment cultures may be derived directly from a local wastewater treatment plant, and other enrichments of AOA and AOB, including other AOB known to produce $N_2O$ and also known to lack the gene needed for reduction of $N_2O$ to $N_2$ may be grown in both pure and mixed cultures in a lab-scale bioreactor system. An example of such an organism is the recently sequenced *Nitrosomonas europaea*. More generally, the bioreactor may use communities of autotrophic microorganisms such as those capable of nitrifier denitrification, ammonia oxidizing bacteria (AOB), and/or ammonia oxidizing archaea (AOA). In other embodiments, the bioreactor may use communities of heterotrophic denitrifying microorganisms either alone or together with communities of autotrophic microorganisms.

Multiple designs for the bioreactor system may be used, including a sequencing batch reactor and an attached growth fluidized bed reactor. In one embodiment, two dispersed growth chemostat reactors are operated in series and equipped for temperature and pH control. As shown in FIG. 2, the first chemostat 206 is operated for partial nitrification (i.e., $NO_2^-$ generation), while the downstream reactor 208 is optimized for maximal $N_2O$ production via nitrifier-denitrification. Details of bioreactor design can be determined from a model of the bioreactor system that integrates reaction stoichiometry and energetics with chemostat mass balances and empirical kinetic coefficients.

For example, based on simulations performed with such a model, the first chemostat in the lab-scale system may initially be provided with high ammonium synthetic wastewater feed, representative of anaerobic digester supernatant or some industrial wastewaters. Low levels (~1 mg/L) of dissolved oxygen (DO) may be maintained in this reactor to select against NOB. $O_2$ delivery may be accomplished using pressurized $O_2$ delivered through hollow fiber membranes. Optimal removal of nitrogen in the second reactor may use a $NO_2^-$:$NH4^+$ ratio in the effluent from the first reactor of approximately 2. A short and tightly controlled residence time (~1.5 days) within the first reactor will enable selection for this ratio, based on the model. The downstream chemostat is operated anoxically, with a residence time of approximately 5 days, based on the model simulations, in order to maximize $N_2O$ production while selecting against slow growing anammox bacteria. Process variables to be evaluated for this type of bioreactor system include $NH_4^+$ loading rate, temperature (20-35), pH (6-8), DO, and hydraulic residence time in each reactor. Monitoring of community structure may be performed using periodic clone libraries and routine monitoring of terminal restriction fragment length polymorphisms and abundance of the same genes using known methods. Levels of NH4+ may be monitored with an NH4+ probe, and nitrite by ion chromatography. Gas phase $N_2O$ production may be monitored using a gas displacement meter with off-line analysis of gas composition on a GC-ECD.

Figure 10A:
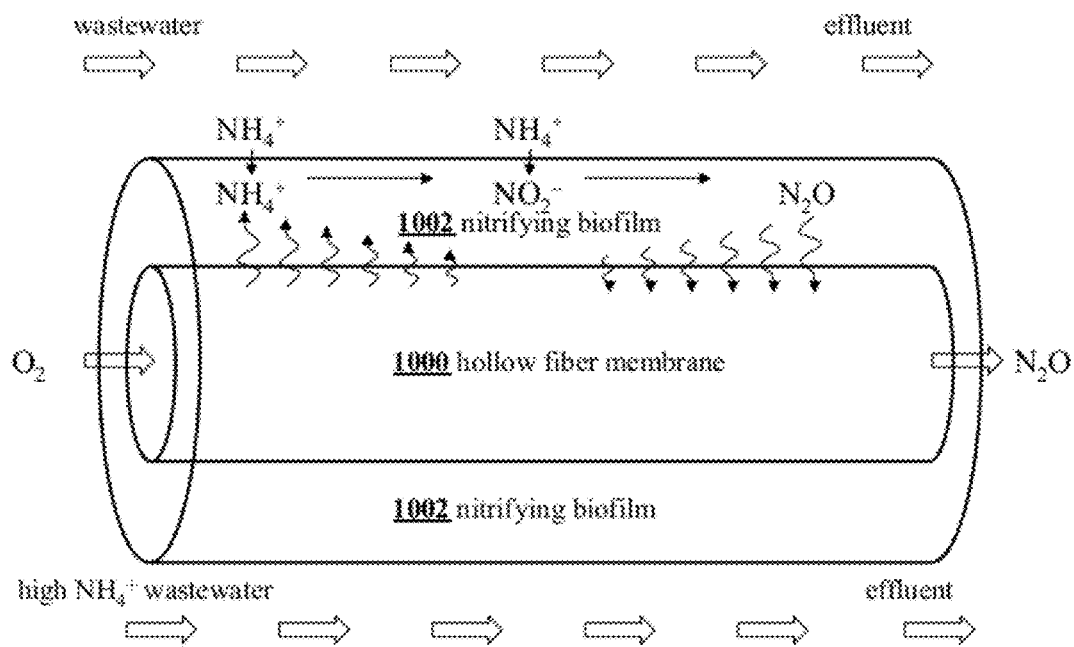
FIG. 10A is a schematic diagram of a hollow fiber membrane bioreactor design according to an embodiment of the invention.
Figure 10B:
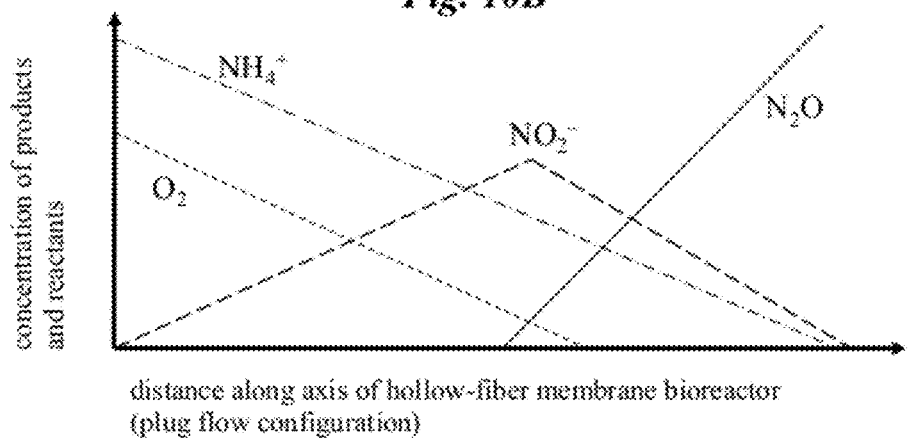
FIG. 10B is a graph illustrating the variation in the concentration of products and reactants with respect to the longitudinal distance along the axis of the hollow fiber membrane bioreactor shown in FIG. 10A.

FIG. 10A is a schematic diagram of a hollow fiber membrane bioreactor design according to an embodiment of the invention. Ammonia removal from wastewater is accomplished in a hollow-fiber membrane bioreactor via a "short-circuit" nitrogen (N) removal bioprocess. $O_2$ or air is supplied to one end of the hollow fiber 1000. The process relies on $O_2$ transfer out of a hollow fiber to a surrounding biofilm composed of a mixed community of ammonia-oxidizing bacteria and archaea. Bulk wastewater (high $NH_4^+$, low COD) flows past the nitrifying biofilm 1002. Oxygen is limited such that the bulk liquid and outer biofilm remain anoxic, and nitrite-oxidizing bacteria are outcompeted. $NO_2^-$ thus initially accumulates. In plug flow operation, the downstream portion of the hollow fiber and the surrounding biofilm is $O_2$ poor. Nitrifier-denitrification promotes additional ammonia oxidization, with nitrite as the terminal electron acceptor, thus leading to $N_2O$ accumulation. $N_2O$ transfers to the lumen of the hollow fiber, replacing oxygen that has exited the fiber, and is captured for catalytic decomposition. High quality (low $NH_4^+$) water is obtained at the reactor effluent. The resulting concentration profiles normal to the membrane wall are shown in FIG. 10B. This graph illustrates the variation in the concentration of products and reactants with respect to the longitudinal distance along the axis of the hollow fiber membrane bioreactor shown in FIG. 10A.

Figure 11:
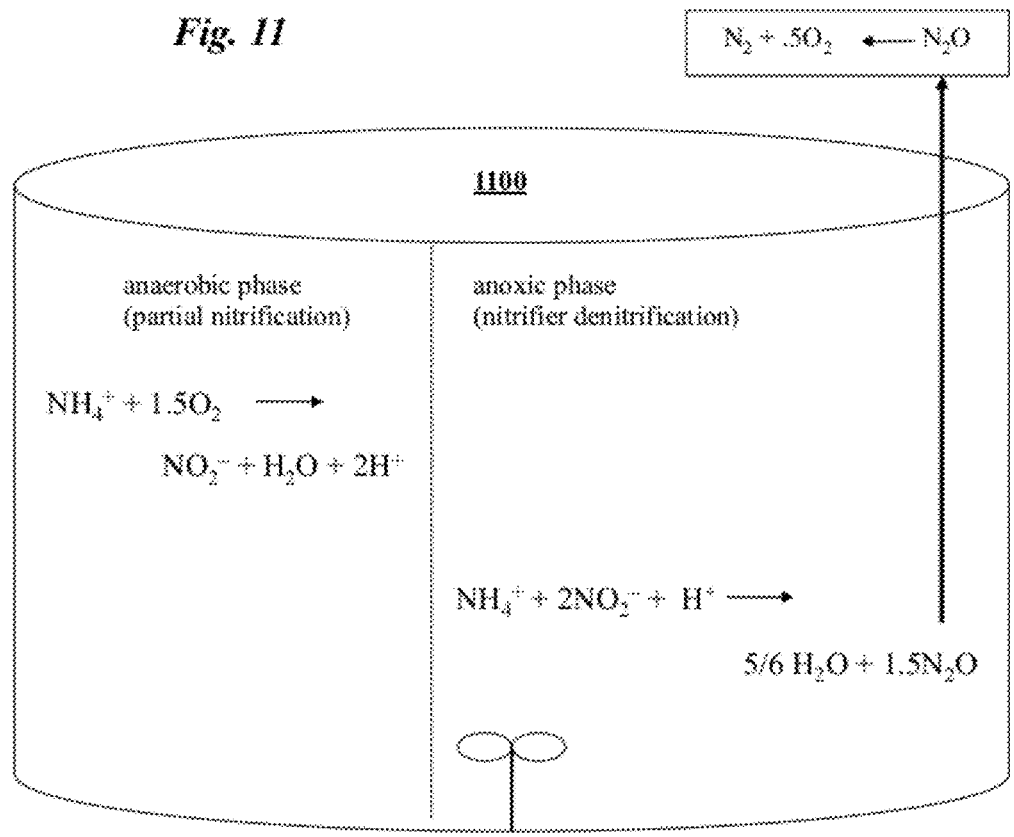
FIG. 11 is a schematic diagram of a sequencing batch reactor with coupled nitrification and nitrifier denitrification according to an embodiment of the invention.

In another embodiment, FIG. 11 shows a sequencing batch reactor 1100 with coupled nitrification and nitrifier denitrification. Ammonia removal from wastewater is accomplished in a sequencing batch reactor (SBR) via a "short-circuit" nitrogen (N) removal bioprocess that alternates between two phases:

I. Anaerobic Phase: Partial nitrification (microbial oxidation of ammonia to nitrite with concomitant reduction of oxygen, as indicated) is promoted. This phase relies on the activity of a mixed community of naturally occurring ammonia-oxidizing bacteria (AOB) and archaea (AOA). Nitrite oxidizing bacteria (NOB) are selected against in this phase via operation at elevated temperature and low dissolved oxygen (DO), thus preventing accumulation of nitrate. Residence time is designed such that about ⅔ of influent ammonia is oxidized to nitrite in this phase. In this anaerobic phase for partial nitrification, $NH_4^+ + 1.5O_2 \Rightarrow NO_2^- + H_2O + 2H^+$.

II. Low Oxygen Phase: While nitrite is typically the end product of microbial ammonia oxidation, under certain conditions (notably low DO), at least some AOB (and possibly AOA) are capable of generating $N_2O$, with nitrite as their terminal electron acceptor-in effect, "breathing" nitrite via the "nitrifier-denitrification" pathway. Phase II of the SBR operation takes advantage of this metabolism to promote $N_2O$ generation from the remaining unoxidized ammonia, thereby reducing nitrite accumulated in phase. Aeration is decreased to low levels, ideally just enough to permit oxidation of ammonia to hydroxylamine: $NH_3 + 0.5O_2 = NH_2OH$. This is followed by oxidation of hydroxylamine with coupled reduction of nitrite to nitrous oxide: $NH_2OH + HNO_2 = N_2O + 2H_2O$. These conditions of low oxygen are maintained to promote maximum production of $N_2O$. The two reactor phases are followed by a gas separation step and catalytic $N_2O$ decomposition. Per standard operating procedures for SBRs, high quality (low $NH_4^+$) effluent is drawn off of the reactor after a biomass settling period. In this anoxic phase for nitrifier denitrification, $NH_4^+ + 2NO_2^- + H^+ \Rightarrow \frac{5}{8}H_2O + 1.5N_2O$.

Figure 12:
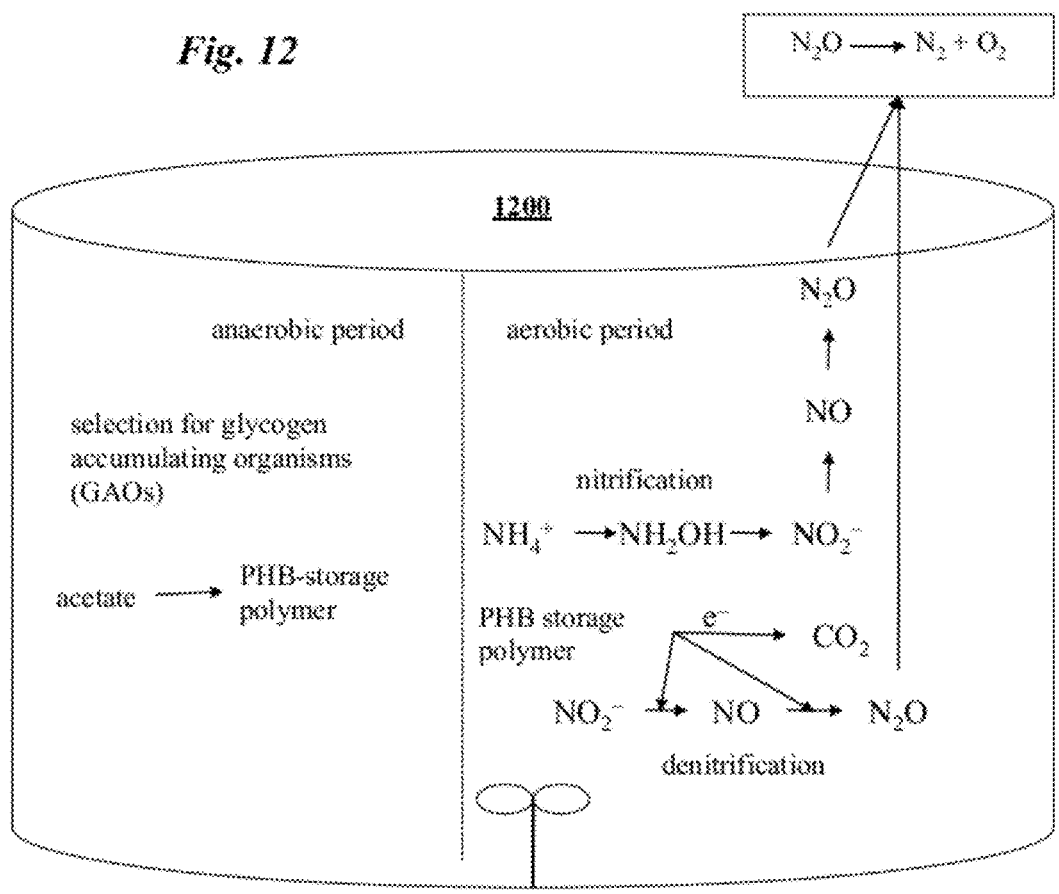
FIG. 12 is a schematic diagram of a sequencing batch reactor which generates a storage polymer in an anaerobic phase and performs nitrification and denitrification in an aerobic period, according to an embodiment of the invention.

FIG. 12 illustrates another embodiment using a sequencing batch reactor 1200. In this embodiment, during an anaerobic phase there is selection for glycogen accumulating organisms (GAOs), generating a PHB storage polymer. In an aerobic period, nitrification and denitrification take place, with the PHB polymer acting as an electron donor for the denitrification as will be described in more detail with reference to FIG. 15, below.

Figure 13:
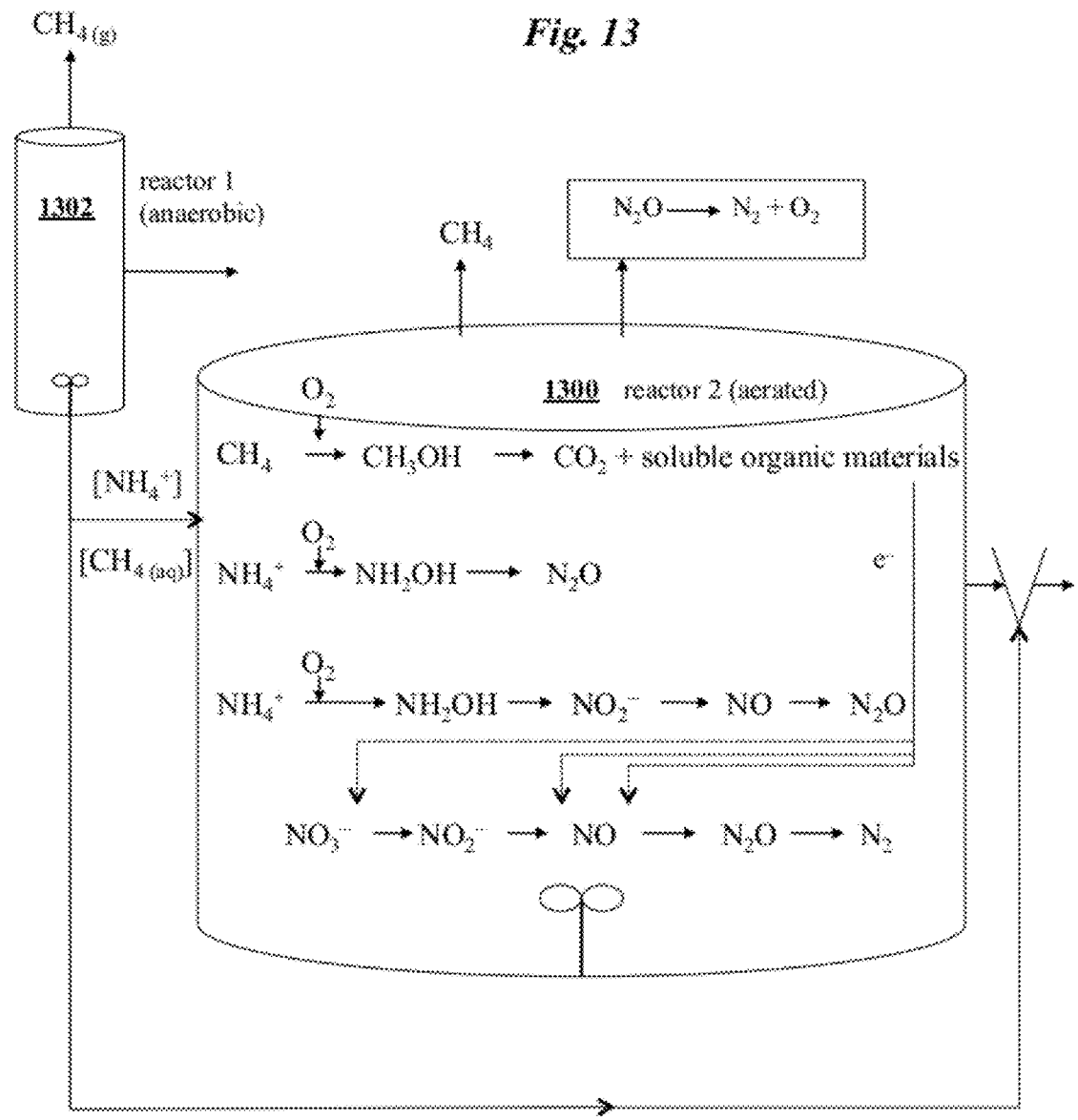
FIG. 13 is a schematic diagram of an embodiment of the invention employing nitrification and methane-driven or organic-driven denitrification.
Figure 14A:
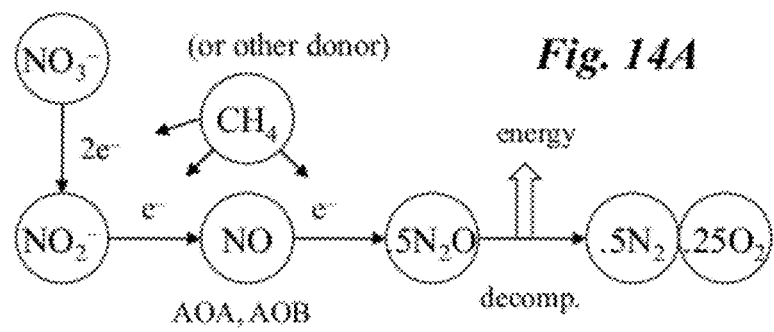
FIGS. 14A-B illustrate energy reactions which take place in the methane-driven or organic-driven denitrification taking place in the device of FIG. 13.
Figure 14B:
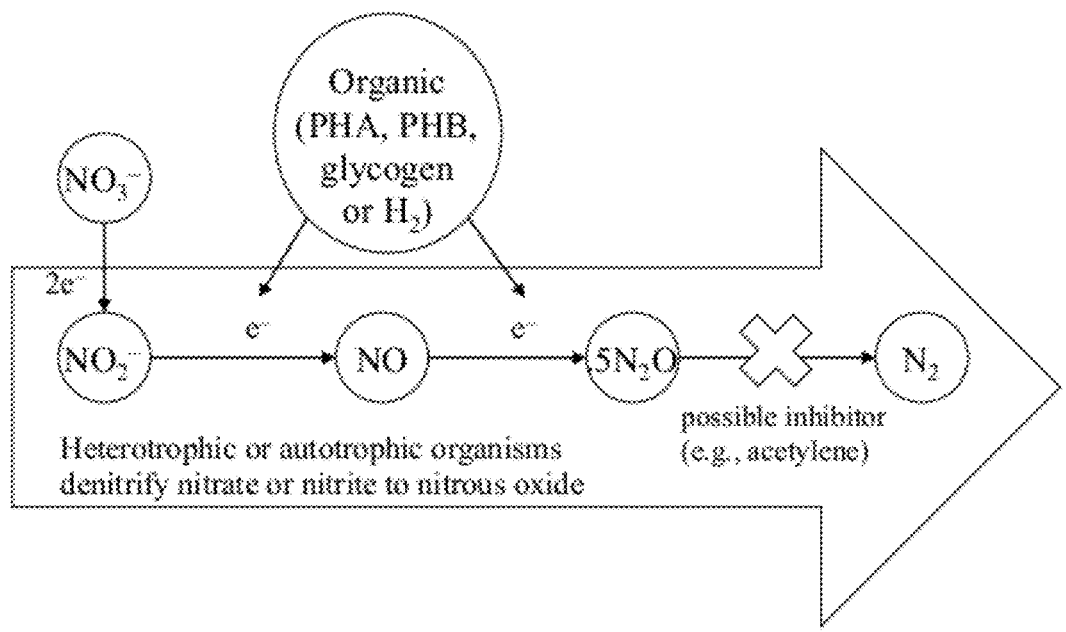

FIG. 13 illustrates another embodiment in which organic materials act as electron donors. In a first reactor 1302 operated anaerobically, methane is produced in both gaseous and dissolved forms. The effluent from this reactor flows into a second reactor 1300 where nitrification and methane-driven denitrification take place, producing $N_2O$ and $CH_4$ gas. Other organics may also be used as electron donors in analogous embodiments, in which partial denitrification follows the pathway shown in FIGS. 14A-B.

Effluent methane concentrations of 10-15 mg/L are typical, constituting about 40-60 mg COD as $CH_4$/L. For typical sewage, this means as much as 20% of total BOD can leave the system as dissolved methane. Ammonium ($NH_4^+$) is also a major component in the effluent of anaerobic reactors. This embodiment provides a system for the removal of nitrogen and soluble organic carbon from the effluent of an anaerobic reactor. In this design, the second reactor 1300 is aerated to maintain low concentrations of dissolved oxygen (DO). Dissolved gaseous products from the microbial transformation of $NH_4^+$ are stripped from the second reactor and captured in a decomposition cell.

The second reactor 1300 combines multiple microbial processes with different metabolic requirements. One pathway involves the metabolism of methanotrophic organisms, which generate energy by oxidation of methane to carbon dioxide ($CO_2$). The first step in the oxidation of methane is carried out by the enzyme methane monooxygenase (mmo). In another pathway, the metabolism of ammonia oxidizing microorganisms that carry out nitrification takes place. The enzyme, ammonia monooxygenase (amo), a structurally similar protein to mmo, catalyzes the first step in the oxidation of $NH_4^+$. The bottom pathway involves denitrification, a microbial process in which nitrate ($NO_3^-$) or nitrite ($NO_2^-$) is reduced to $N_2$ gas, with nitric oxide (NO) and nitrous oxide ($N_2O$) as intermediate products. Some denitrifying organisms, which may be numerically dominant within a denitrifying reactor, carry out partial denitrification, such that $N_2O$ (and not $N_2$) is the final product of metabolism.

There is overlap in the metabolic reactions of methanotrophic, nitrifying, and denitrifying microorganisms. For instance, the second pathway describes the possible co-metabolism of $NH_4^+$ by methantrophic organisms. Due to relaxed substrate specificity, the mmo enzyme has been shown to oxidize $NH_4^+$ as well as its intended target $CH_4$. The result of this co-metabolic transformation is hydroxylamine, the desired substrate for $N_2O$ formation when coupled with nitrite reduction. Methanotrophs are unable to extract energy from the oxidation of $NH_4^+$.

Ammonia oxidizing organisms can co-metabolize methane. This methanol is also a potential source of electrons for partial denitrification to produce $N_2O$. Under oxygen limiting conditions, other soluble products of methanotrophic metabolism, such as acetate, can also form and may serve as electron donors. In sum, the system described in FIG. 13 is to be optimized for the removal of dissolve methane and conversion of $NH_4^+$ to $N_2O$.

Figure 15:
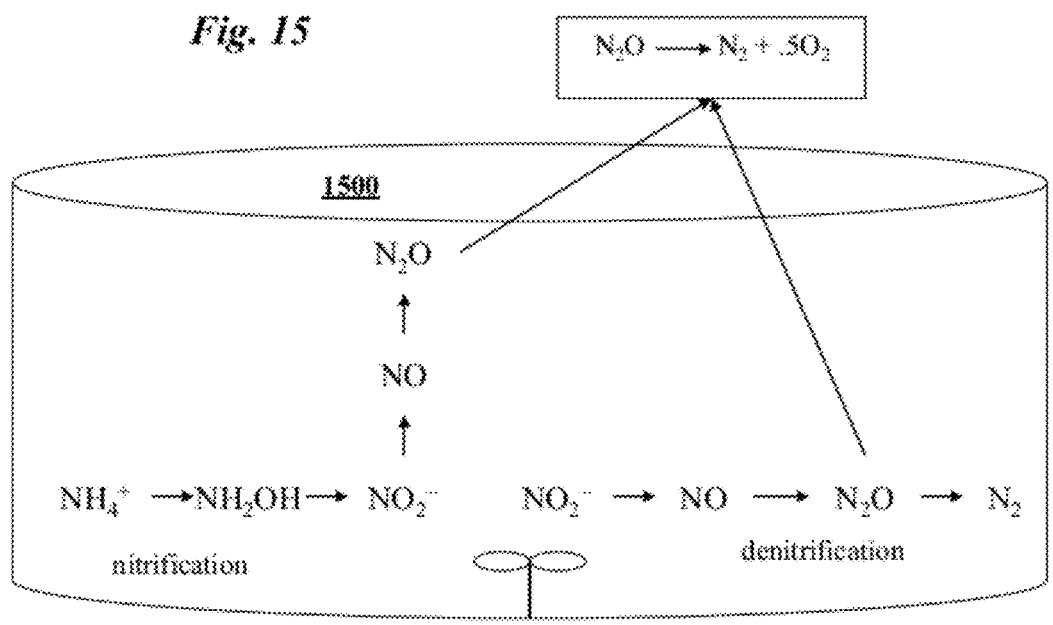
FIG. 15 is a schematic diagram of a micro-aerated bioreactor for simultaneous nitrification and denitrification according to an embodiment of the invention.

FIG. 15 shows another embodiment which employs a micro-aerated bioreactor 1500 for simultaneous nitrification and denitrification (SND). This figure illustrates nitrification-denitrification in which two different microbial processes (involving two distinct groups of organisms) occur simultaneously within a single reactor. In some other embodiments, the conversion of ammonia to nitrous oxide relies exclusively on ammonia oxidizing bacteria (AOB). By contrast, a SND reactor achieves the same transformation of nitrogen, but makes use of both autotrophic nitrifying and heterotrophic denitrifying organisms. Intracellular storage polymers (e.g., glycogen or polyhydroxybutyrate) provide the reducing equivalents needed for partial denitrification of nitrite to $N_2O$. SND reactors can function under a number of operational configurations. For instance, SND can occur in a sequencing batch reactor, where operational conditions shift between oxic and anoxic conditions. SND may also occur when oxygen remains present in the bulk reactor liquid. Bacteria in a reactor can clump into flocs, introducing mass transfer limitations. Oxygen concentration gradients formed within the microbial floc create a niche for denitrifying organisms within an aerated reactor. Nitrous oxide can be produced as a product of both processes.

SND may be successfully combined with other nutrient removal strategies such as phosphorous removal. In these combined processes high levels of partial denitrification (emission of $N_2O$ instead of $N_2$) may be observed. Furthermore, high levels of $N_2O$ emission in nitrifying and denitrifying reactors may take place under dynamic process controls cycling between oxic and anoxic conditions. Such a scheme is shown in FIG. 12.

Figure 17A:
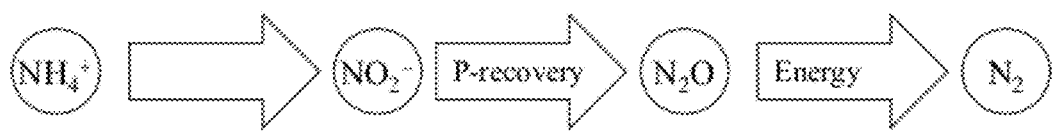

The inventors have discovered that organisms may produce $N_2O$ through incorporation and subsequent oxidation of PHB (Polyhydroxybutyrate) within the cell. This is quite significant as it suggests a mechanism by which organisms may produce high levels of $N_2O$ and provides an avenue for phosphorus recovery (a valuable nutrient in wastewater). In such an enhanced biological phosphorus removal (EBPR) technique, the denitrification to $N_2O$ occurs through incorporation and oxidation of endogenous carbon including PHA. This new EBPR technique is based on the discovery that phosphorus may be recovered by heterotrophic denitrifying organisms that reduce nitrite to nitrous oxide or by other organisms that are present in the $N_2O$ producing bioreactor with cycling anaerobic and anoxic phases. The denitrifying organisms have been observed to accumulate poly-phosphate (poly-P), a phosphorus-containing granule incorporated into the cell and associated with the oxidation of Polyhydroxyalkanoates (PHA), an intracellular carbon source. In operational modes with transient feeding regimes, the organisms have been observed to accumulate PHA and reduce nitrite to nitrous oxide. This particular mechanism provides a pathway for the recovery of phosphorus and nitrogen waste as energy in the form of $N_2O$ by swapping of nitrite for oxygen in the conventional EBPR process. These embodiments involving EBPR meet longstanding needs by removing both nitrogen and phosphorus from wastewater while generating renewable energy. It provides a sustainable biological method for the recovery of phosphorus without the need for large quantities of chemicals. EBPR removes phosphorus through alternating anaerobic and aerobic stages in which phosphate is incorporated into cell biomass in the form poly-phosphate (poly-P). Cells are then removed and phosphorus is recovered as poly-P. Conventional EBPR imposes an oxygen demand on wastewater treatment and does not provide a pathway for treating nitrogen waste. The present invention can enhance EBPR by changing the aerobic stage for an anoxic stage with nitrite. This alteration enables recovery of phosphorus, removal of waste nitrogen, recovery of energy from nitrogen waste, and lowers the energy demand of EBPR by reducing or removing aeration. FIG. 17A shows the general processing of nitrogen, where phosphorus recovery (P-recovery) and energy recovery from waste nitrogen take place in the second and third steps, respectively.

Figure 17B:
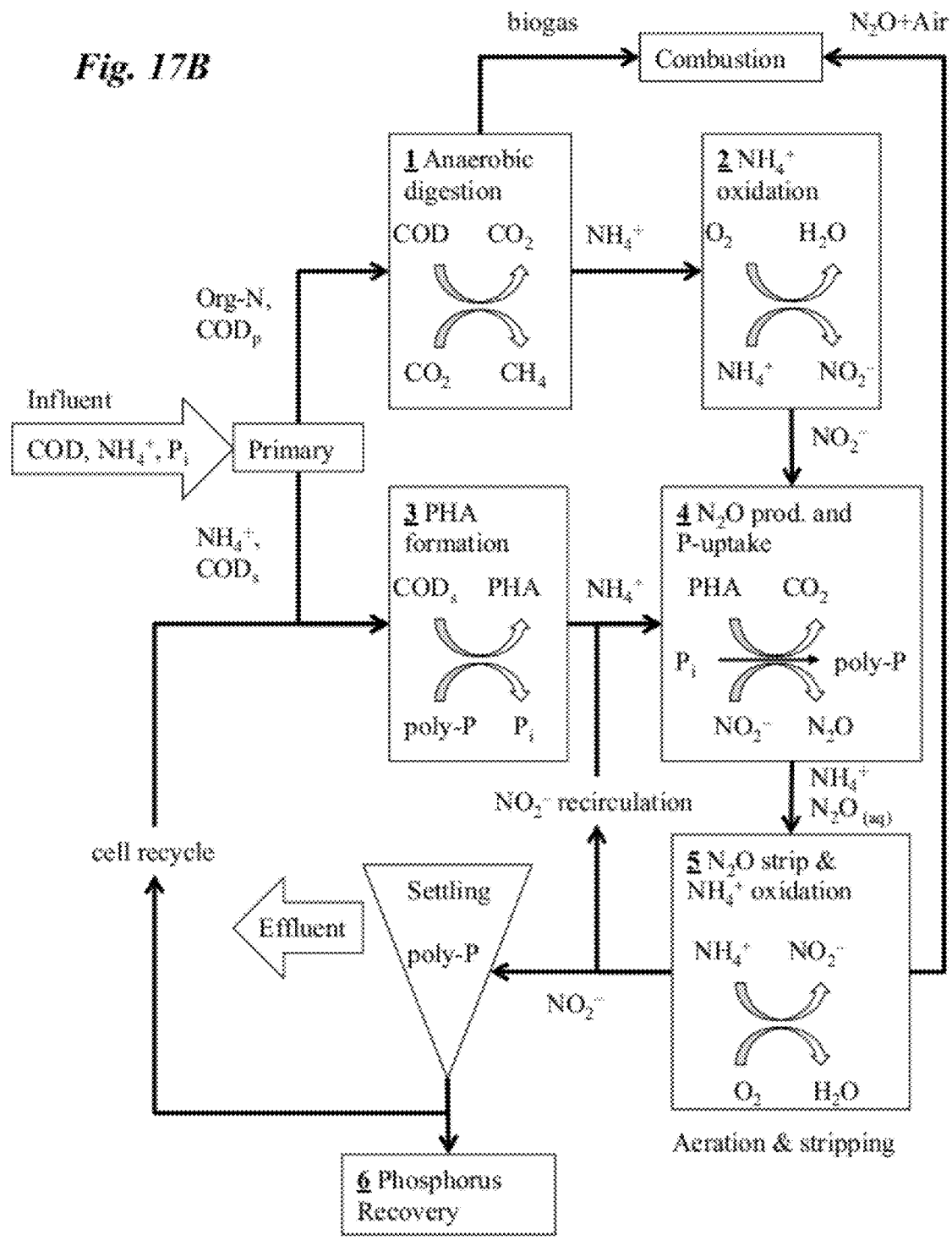

FIG. 17B is a schematic diagram illustrating one embodiment of the invention performing EBPR. Influent wastewater containing nitrogen, organics, and phosphorus is processed to recover energy and phosphorus. The process steps are detailed as follows:

1. Particulate organic matter is digested anaerobically to produce biogass ($CH_4$ and $CO_2$) that can be burned to recovery energy.
2. Ammonia from the anaerobic digester centrate is oxidized to nitrite.
3. Soluble organic matter (i.e. volatile fatty acids, acetate) is consumed by the phosphate accumulating denitrifying organisms to convert polyphosphate (poly-P) to PHA within the cells and release inorganic phosphorus (Pi).
4. PHA is oxidized to reduce nitrite to nitrous oxide. Inorganic phosphorus is incorporated into the cell and converted into polyphosphate.
5. Dissolved nitrous oxide is stripped out of solution and energy is recovered from $N_2O$ decomposition and/or combustion. Remaining soluble ammonia is partially oxidized to nitrite and recirculated back to anoxic phosphorus uptake stage to be reduced to nitrous oxide.
6. A fraction of the recycled cells are wasted and phosphorus is recovered as polyphosphate granules within the cells.

Nitrite reduction to nitrous oxide with cellular phosphorus accumulation has been experimentally demonstrated by the inventors with synthetic wastewater to provide 62% conversion of nitrite to nitrous oxide with Polyhydroxybutyrate (PHB) accumulation, with partial denitrification of nitrite to nitrous oxide with phosphorus uptake. The inventors demonstrated 80-85% conversion of nitrite to nitrous oxide over repeated cycles in a bioreactor system treating real anaerobic digester filtrate.

In embodiments of the invention, partial anoxic reduction of $NO_2^-$ to $N_2O$ may be implemented in several different ways. According to one approach, chemical oxygen demand (COD) stored as polyhroxybutyrate (PHB) is used as the electron donor for partial heterotrophic reduction of $NO_2^-$ to $N_2O$. For partial heterotrophic denitrification, different selection conditions may be imposed on acetate- and nitrite-fed communities initially derived from waste activated sludge. In experiments, no $N_2O$ was detected when acetate and nitrite were supplied continuously, but $N_2O$ was produced when acetate and nitrite were added as pulses. When acetate and nitrite were added together (coupled feeding), $N_2O$ conversion efficiency was 9-12%, but when acetate and nitrite additions were decoupled, $N_2O$ conversion efficiency was 60-65%. It was found that decoupled substrate addition selected for a microbial community that accumulated polyhydroxybutyrate (PHB) during an anaerobic period after acetate addition, then consumed PHB and reduced $NO_2^-$ during the subsequent anoxic period.

This approach for partial heterotrophic denitrification is based on a review of factors previously implicated in $N_2O$ production by denitrifying heterotrophs: (1) low COD/N, (2) high nitrite levels, (3) transient feeding regimes (i.e. feast and famine), (4) low pH (i.e. high concentration of free nitrous acid), and (5) low dissolved oxygen. In general, more extensive conversion to $N_2O$ was associated with: (1) limited availability of COD; (2) oxidation of endogenous COD in pulse fed systems; or (3) inhibition of $N_2O$ reduction at high $NO_2^-$ levels.

A decoupled feeding regime may be used to select for organisms that store PHB and use it as the source of reducing equivalents for nitrite reduction. The efficiency of nitrogen removal from the water may be 98%, with 62% conversion of $NO_2^-$ to $N_2O$.

Iron

Figure 16A:
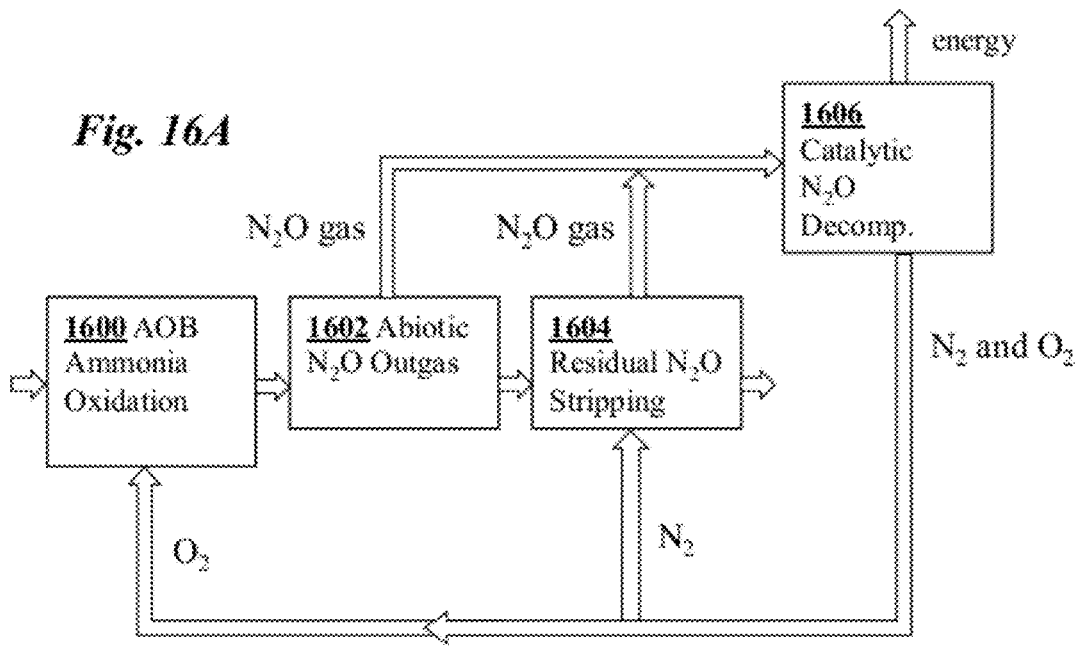
FIGS. 16A-C illustrate pathways used in an embodiment of the invention where abiotic Fe(II)-mediated reduction of nitrite to nitrous oxide.
Figure 16B:
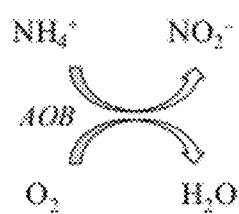
Figure 16C:
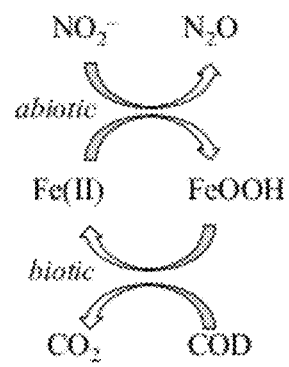

In some embodiments of the invention, the reactors use alternative processes to perform partial reduction of nitrite to nitrous oxide ($N_2O$) in gas and aqueous phase. According to one embodiment, the processing of the nitrogen compounds to produce the nitrous oxide may include abiotic Fe(II)-mediated reduction of nitrite to the nitrous oxide and Fe(III); and regenerating Fe(II) from Fe(III) using iron-reducing bacteria. Abiotic Fe(II)-mediated reduction of nitrite to $N_2O$. As depicted in FIG. 16A, AOB ammonia oxidation takes place in step 1600, followed by abiotic nitrous oxide outgas in step 1602. In step 1604 residual nitrous oxide is stripped using nitrogen gas, and the nitrous oxide from steps 1602 and 1604 are fed to catalytic decomposition reactor 1606 where energy is produced along with nitrogen and oxygen gas, which are fed back to steps 1604 and 1600, respectively. FIG. 16B illustrates ammonia oxidation by AOB in step 1600, while FIG. 16C illustrates step 1602 where Fe(II) reacts with nitrite to produce $N_2O$ and Fe(III). Iron-reducing bacteria, such as Geobacter or Methanotrophs can couple oxidation of carbon containing compounds, such as acetate or methane, to reduction of Fe(III), thereby regenerating the Fe(II). Alternatively, waste Fe(II) may be added as a process input. $FeCl_2$ is a waste product of the steel industry, termed "spent pickle liquor", and already used in many wastewater treatment facilities for phosphate removal.

In another embodiment, the reduction of nitrite to nitrous oxide ($N_2O$) may include microbial reduction of nitrite to nitrous oxide using organics as an electron donor, e.g., using acetate or polydroxyalkanoate granules from *Alcaligenes faecalis*. This approach exploits the capability of *Alcaligenes faecalis* and related organisms to reduce nitrite to $N_2O$ using acetate or polydroxyalkanoate granules as the electron donor.

As another alternative, the processing in the bioreactor system of the nitrogen compounds to produce the nitrous oxide may include microbial oxidation of ammonia coupled to Fe(III)-reduction followed by abiotic reaction of nitrite with Fe(II) to nitrous oxide, e.g., using Feammox bacteria to couple ammonium oxidation to nitrite with reduction of Fe(II) to Fe(III). This approach involves microbial oxidation of ammonia with coupled to Fe(III) reduction followed by abiotic reaction of nitrite with Fe(II) to $N_2O$. This approach enables production of $N_2O$ without oxidation of organic matter, increasing the organic matter that may be converted to methane in an upstream anaerobic process.

The above two embodiments involving iron may also provide the benefit that they remove phosphorus as iron precipitate ($FePO_4$) and improve metals removal through sorption or co-precipitation with Fe(III) solids. These embodiments take advantage of the fact that Fe (II) species react abiotically with nitrite to form nitrous oxide. The coupled oxidation of ferrous iron with nitrite reduction results in ferric iron precipitate. Reduction of ferric iron back into ferrous iron may be used to establish an iron cycle in the system and avoid the need for external input of Fe(II). One method for establishing a ferric/ferrous iron cycle is the embodiment described above in which iron reducing organisms are used to regenerate Fe(II). These organisms are fast growing, highly robust, and well characterized. In this configuration, part of the soluble COD effluent from primary treatment could be used as reducing power for ferric reduction. This configuration would enable batch operation with a two-step cycle: (1) ferric iron reduction to ferrous iron followed by (2) ferrous iron oxidation with nitrite reduction to nitrous oxide. The other embodiment above can also maintain an iron cycle by reducing ferric iron with ammonia oxidation with use of the Feammox organisms. Furthermore, ammonia oxidation couple to ferric iron reduction is thermodynamically favorable at typical pH values and reactant concentrations when ferrous iron concentration is low. This strategy is simpler and uses no COD; freeing up additional COD for methane production and enabling nitrite conversion to nitrous oxide in a single step.

Separation and Concentration of Nitrous Oxide

Figure 5A:
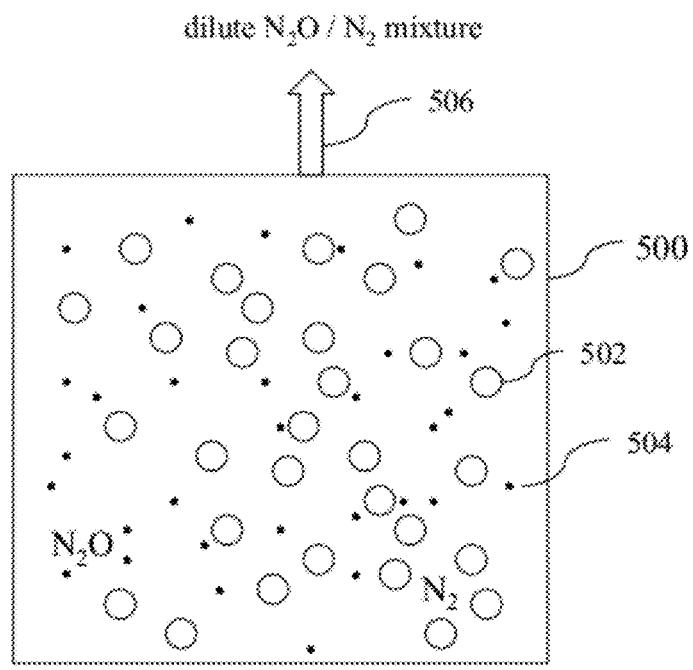
FIG. 5A is a schematic diagram of a gas stripping column for separating $N_2O$ dissolved in an effluent to produce gaseous $N_2O$ according to an embodiment of the invention.
Figure 5B:
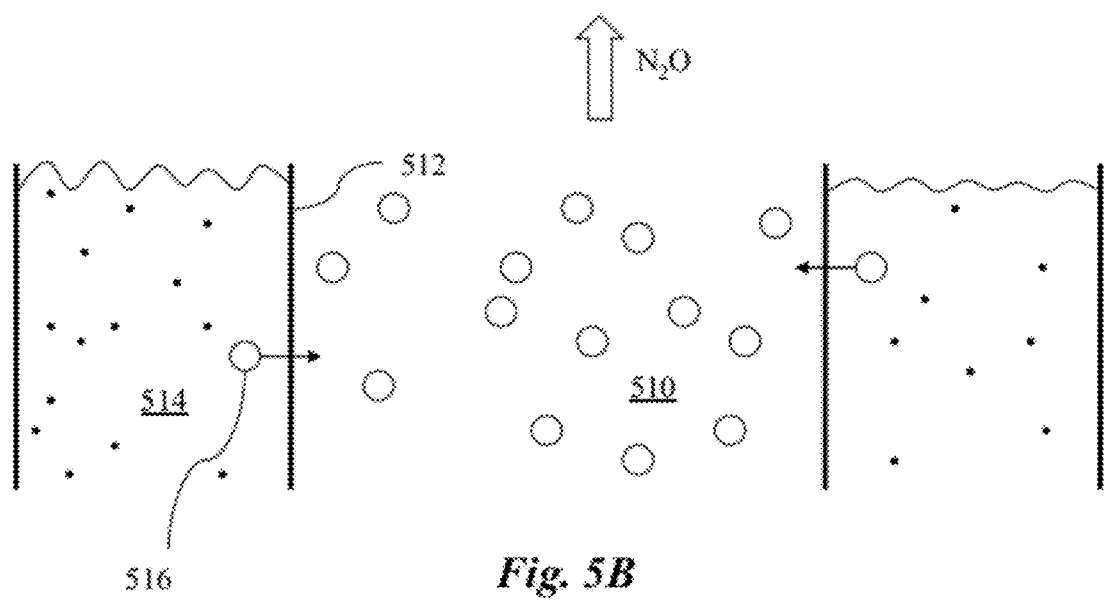
FIG. 5B is a schematic diagram of a gas separation device using pervaporation for separating $N_2O$ dissolved in an effluent to produce gaseous $N_2O$ according to an embodiment of the invention.

The nitrous oxide product from the bioreactor may be processed in various ways prior to chemically reacting in gas phase in the hardware device. Under the high influent $NH4^+$ levels in this type of bioreactor system, a high vapor pressure of $N_2O$ (50.8 atm at 20° C.) is expected to enable direct capture of $N_2O$ from the headspace of the second chemostat for decomposition and power generation. However, due to the relatively high solubility of $N_2O$ in water (1.08 g/l at 25° C. and 1 atm) it may be desirable to include a separation mechanism 204 to promote near-complete partitioning of dissolved $N_2O$ from the aqueous effluent to increase the portion of gas phase $N_2O$. Consequently, the method may include using a separator (204, FIG. 2) for separating a portion of the nitrous oxide that is dissolved in aqueous effluent from the bioreactor to increase an amount of gas phase of the nitrous oxide product to provide efficient mass transfer of biologically produced $N_2O$ from aqueous to a contained gas phase. Various techniques may be used to accomplish this end. For example, a small gas stripping column 500 may be used, as shown in FIG. 5A. In the column, $N_2$ carrier gas bubbles 502 are introduced to the solution containing dissolved $N_2O$ 504. The $N_2$ bubbles 502 strip the $N_2O$ 504 from the solution and the $N_2/N_2O$ gas mixture 506 may then be captured as the bubbles emerge from the top of the column. At 25° C., gas-phase $N_2O$ can be separated from $N_2$ carrier gas by a molecular sieve, and $N_2$ gas may be recycled back to form new bubbles at the bottom of the stripping column. Alternatively, a separator may be implemented using vacuum separation from the second chemostat reactor, as shown in cross-sectional view in FIG. 5B. A central column 510 with a vacuum is separated a permeable membrane 512 selective for $N_2O$ from an annular column 514 containing effluent with dissolved $N_2O$ 516. Through pervaporation, dissolved $N_2O$ is directly extracted from the effluent as it passes through the membrane 512 and into the central column 510.

Figure 6:
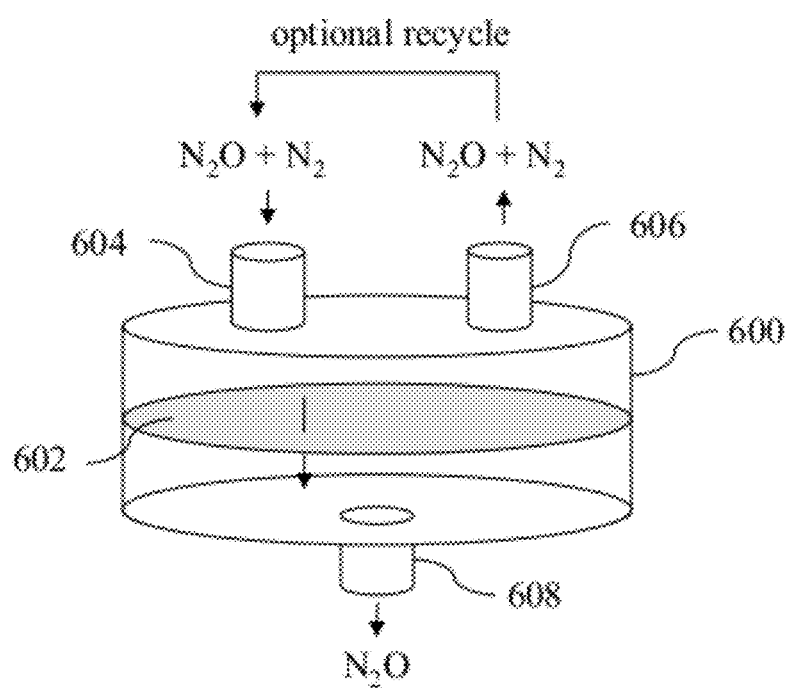
FIG. 6 is a schematic diagram of a device for concentrating $N_2O$ in a gas stream according to an embodiment of the invention.

In some embodiments, it may be desirable to concentrate the amount of the gas phase nitrous oxide in the gas stream prior to entering the chemical reactor. For example, FIG. 6 shows one possible implementation of a device for concentrating $N_2O$ in a gas stream. The device has a chamber 600 divided into upper and lower subchambers by a selective membrane 602. A mixture of $N_2O$ and $N_2$ enters the upper subchamber through a port 604 and exits through a port 606. $N_2O$ gas in the upper subchamber selectively passes through the membrane 602 into the lower subchamber and exits through port 608, producing a concentrated stream of $N_2O$ gas. The $N_2O$ can alternatively be concentrated using various other techniques.

Decomposition of Nitrous Oxide Gas

In a preferred embodiment, the gaseous nitrous oxide is decomposed to produce nitrogen gas and oxygen gas in the hardware reactor device designed to operate at the outlet conditions of the bioreactor. The decomposition may be performed in various ways such as catalytically, thermally by external heating, or through exothermic decomposition. This decomposition reaction, when combined with the $N_2O$ generating bioreactor system in embodiments of the invention, produce a new source of renewable energy and, since the product of the decomposition reaction is oxygen-enriched air, this energy is generated with zero production of greenhouse gas. Moreover, the $O_2$ product from the nitrous oxide decomposition can be recycled back to the bioreactor system, offsetting a significant fraction of the oxygen demand for the partial ammonia oxidation needed to produce $N_2O$ from ammonia.

Figure 7:
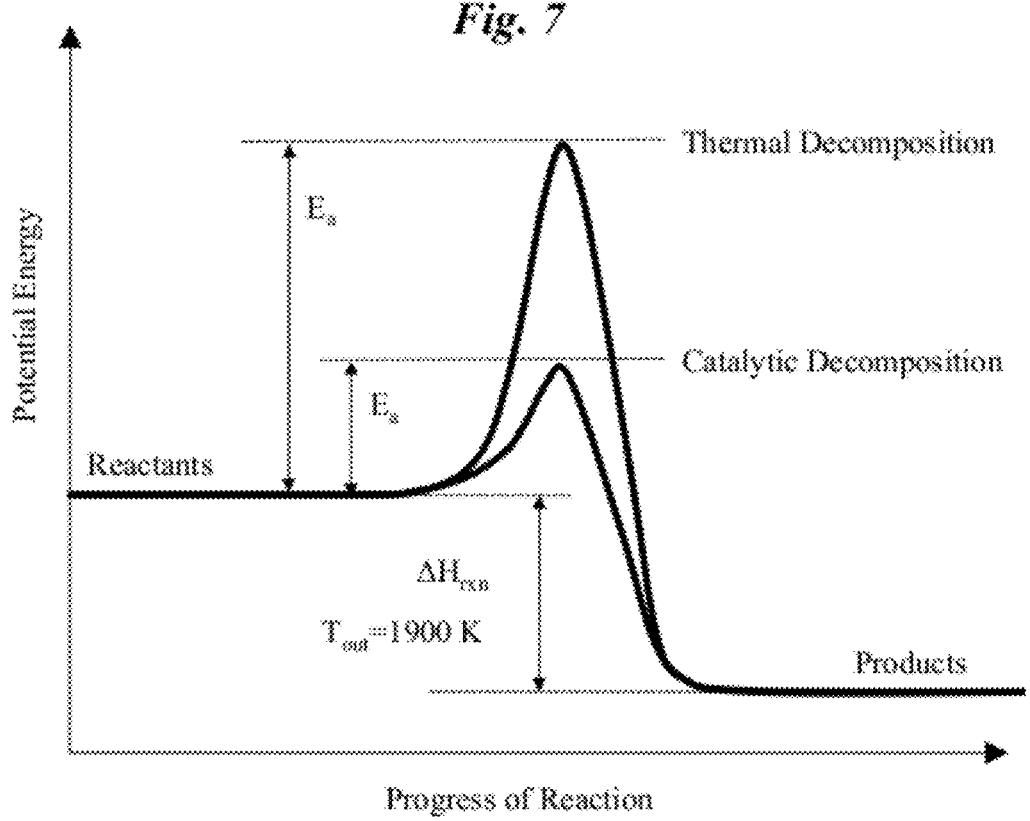
FIG. 7 is a graph of energy vs. reaction progress for the decomposition reaction $N_2O \rightarrow \frac{1}{2}O_2 + N_2 + 82$ kJ, contrasting the thermal dissociation with the catalytic dissociation as employed in an embodiment of the present invention.

The global decomposition reaction for $N_2O$ is exothermic. The energy diagram for the reaction $N_2O \rightarrow \frac{1}{2}O_2+N_2+82\,kJ$ is shown in FIG. 7. This decomposition reaction reaches appreciable rates at temperatures over 850° C. and is initiated by an activation energy of approximately 250 kJ/mol. However, this activation energy can be significantly reduced in the presence of a metal catalyst such as rhodium and/or very lean concentrations of methane. It should be noted that small amounts of hydrocarbon or hydrogen in $N_2O$ can greatly increase the rate of decomposition. A properly designed and well-characterized system can safely operate with very lean amounts of methane. Furthermore, the presence of very lean methane concentrations significantly increases the kinetics of $N_2O$ decomposition.

Figure 8:
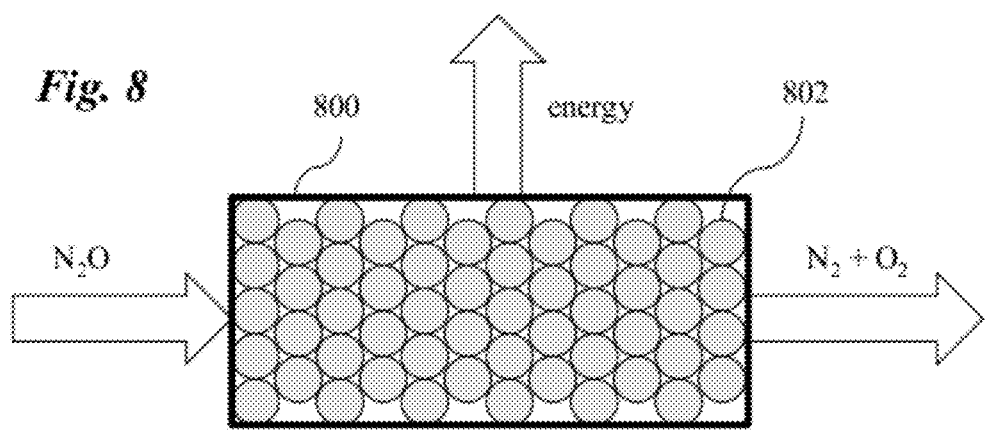
FIG. 8 is a schematic diagram of a hardware reactor device for performing catalytic decomposition of the nitrous oxide according to an embodiment of the invention.

In case the decomposition of the nitrous oxide is performed catalytically, the decomposition may be performed as shown in FIG. 8 by flowing a gas stream containing a suitably high concentration of gaseous nitrous oxide through a chamber 800 containing a catalyst 802, e.g., deposited on spherical particles made of a catalyst support. Once the reaction is started, the energy released is used to keep the catalyst material hot to sustain the reaction. Excess energy may be extracted as heat for power generation, e.g., using a Sterling cycle heat engine. If the concentration of the nitrogen is not sufficiently high, however, the catalyst material may need to be heated externally to sustain the decomposition reaction. An $N_2O$ decomposition device appropriate for use in embodiments of the present invention is preferably capable of sustaining stable and continuous operation in a hot oxidizing environment while minimizing thermal degradation of housing walls. The chamber 800 may be made of a high-temperature ceramic or high-temperature alloy. The catalyst 802 may be a metal or metal oxide, such as a transition metal or transition metal oxide. Catalysts include rhodium, rhodium oxide, iron, or iron oxide. Catalyst supports may include gamma phase aluminum oxide, zeolites, or a high surface area ceramic. Some embodiments of the hardware reactor device may include a built-in ceramic glow plug for preheating the catalyst bed, a Hastelloy-X chamber for high temperature oxidation resistance, and a ceramic yttria-stabilized zirconia aft catalyst bed support. Embodiments may employ high temperature resistant refractory ceramics, such as ceramic matrix composite (CMC) aluminum oxide, that ensure long operational lifetimes with minimal structural degradation. Very lean concentrations of methane may be introduced into the decomposition chamber to increase the decomposition kinetics of $N_2O$ and help maintain decomposition at very low flow rates. Thermal insulation of the device chamber, e.g., with aluminum oxide layers, may be used to minimize decomposition heat loss. Multiple nano-layered coatings may be used to further reduce the thermal conductivity of the insulating material.

In one embodiment, a dilute catalytic decomposition is performed with a small amount of $N_2O$ gas mixed with $N_2$ gas, e.g., 2% and 98%, respectively. The chamber 800 is heated, e.g., by wrapping it in heat tape, and the spherical particles are porous to present to the $N_2O$ a large and hot catalytic surface area. Alternatively, with a very high (e.g., above 90%) concentration of incoming $N_2O$ gas, a self-sustaining catalytic decomposition may take place, without the use of heat tape or other external heating.

Combustion with Nitrous Oxide Gas as Oxidant or Co-Oxidant

In some embodiments of the invention, rather than decomposing the nitrous oxide in the hardware reactor device, it may be used instead as an oxidant or co-oxidant in a combustion reaction, e.g., in the combustion of methane or other fuel. For example, $CH_4+4N_2O \Rightarrow CO_2+2H_2O+N_2+heat$.

Advantages, Wastewater Treatment Example

Embodiments of the invention have numerous advantages over prior methods.

1. This technology could triple the amount of methane that can be recovered at a treatment plant. For municipal sewage, this could be up to about 0.1 L of methane gas per liter of wastewater treated. In contrast to the conventional method of nitrogen removal which uses waste organics for reducing power, the present technology uses ammonia instead of organic matter. Consequently, much more organic matter is available for methane production.

2. The amount of $O_2$ used for nitrification is 60% less that than required by conventional methods. This reduction is significant because aeration is about 50% of the operational costs of a treatment plant.

3. Waste biomass is significantly decreased because heterotrophic denitrification, a process that produces considerable biomass, is no longer necessary. Disposal of waste biomass is the second greatest operational expense at treatment plants.

4. A well-known anaerobic ammonia oxidation technology recently developed at Delft University relies upon anammox bacteria. These are very slow-growing bacteria, and as a result, the reactors are slow to start up, and slow to fix when upset. The organisms used in the present technology, in contrast, are more robust and have shorter doubling times.

5. The small size of the nitrous decomposition reactors is well-suited for compact distributed operation of wastewater systems.

6. Emissions of greenhouse gas $N_2O$ are eliminated through a process that creates an economic incentive for $N_2O$ production and capture—like processes for production and capture of the greenhouse gas methane.

Embodiments of the invention have the potential to dramatically change domestic and industrial wastewater treatment and nitrogen management in landfill leachates. In addition, they can also impact biomass production of biodiesel, ethanol, and other fuels.

In these processes, fuels must be separated from nitrogen-containing biomass, which then becomes waste. Conversion of the waste nitrogen to nitrous oxide enables power production, avoids greenhouse gas emissions, and prevents discharge of other harmful forms of nitrogen.

To illustrate the advantages, consider the Palo Alto Water Quality Control Plant as an example of the potential energy benefits to implementing this technology. An estimated 2000 kg of $N_2O$ could potentially be produced per day by this plant if the treatment plant bioreactors were operated so as to maximize $N_2O$ production. This rate of production (23 grams/sec) of $N_2O$ would generate 43 kW. To put this in perspective, an average home consumes approximately 7 kW-hr per day. Assuming an energy conversion efficiency of 30%, the 43 kW generated by the decomposition of $N_2O$ could power approximately 40 homes. The reactor needed to accomplish this rate of decomposition would only be three to four times the size of the ones developed to date. This translates into even bigger energy generation in wastewater treatment plants such as San Jose where it is estimated that $N_2O$ production via microbial processes could be 10 times greater than that of Palo Alto. The above energy benefits only address the energy available in the nitrogen. Additional energy benefits would derive from the fact that this process, if coupled to methane fermentation for carbon removal, could avoid use of organic matter as a supply of reducing power, thereby allowing increased production of methane. For typical sewage, three times more methane could potentially be generated compared to the conventional wastewater treatment process. Nor does the above energy analysis include the benefit resulting from a significant reduction in oxygen from coupled methane fermentation for carbon removal and $N_2O$ production/decomposition for nitrogen removal. Carried out on a large scale, this technology can be a significant source of renewable energy.

The invention claimed is:

1. A method for wastewater treatment and energy production wherein nitrogen is removed from wastewater and converted to nitrous oxide and wherein energy is produced from the nitrous oxide, the method comprising:
    a) pumping the wastewater into a bioreactor system, wherein the wastewater comprises nitrogen compounds;
    b) processing in the bioreactor system the nitrogen compounds in the wastewater to produce a nitrous oxide product;
    c) forming a nitrous oxide gas stream from the nitrous oxide product of the bioreactor system;
    d) chemically reacting the nitrous oxide gas stream in a hardware reactor device coupled to the bioreactor system to produce energy obtained from the nitrous oxide product of the bioreactor system,
        whereby energy is produced from the nitrogen compounds in the wastewater.

2. The method of claim 1 wherein a first stage of the bioreactor system is an aerobic stage and a second stage of the bioreactor system cycles between anaerobic and anoxic phases, wherein the second stage comprises selection for organisms that generate intracellular storage polymers during an anaerobic phase and perform partial denitrifaction to nitrous oxide driven by oxidation of the endogenous carbon during an anoxic phase.

3. The method of claim 2 wherein the intracellular storage polymers comprise glycogen, PHA, or PHB.

4. The method of claim 2 wherein the organisms are *Comamonas* sp. capable of endogenous carbon storage and partial denitrification to nitrous oxide.

5. The method of claim 1 wherein the processing in the bioreactor system comprises partial denitrification of nitrate or nitrite to nitrous oxide using a nitrous oxide reductase inhibitor to inhibit nitrous oxide reduction to nitrogen gas.

6. The method of claim 5 wherein the nitrous oxide reductase inhibitor is acetylene.

7. The method of claim 1 wherein the nitrogen compounds in the bioreactor system to produce the nitrous oxide comprises microbial reduction of nitrite or nitrate to nitrous oxide using organics as an electron donor.

8. The method of claim 1 wherein processing the nitrogen compounds in the bioreactor system to produce the nitrous oxide comprises microbial reduction of nitrite or nitrate to nitrous oxide using autotrophic organisms capable of autotrophic denitrification.

9. The method of claim 8 wherein the autotrophic organisms utilize hydrogen as an electron donor during denitrification.

10. The method of claim 1 wherein processing the nitrogen compounds in the bioreactor system to produce the nitrous oxide comprises heterotrophic denitrification wherein the denitrification to nitrous oxide is accomplished through incorporation and oxidation of endogenous carbon including PHA or oxidation of methane.

11. The method of claim 1 wherein processing the nitrogen compounds in the bioreactor system to produce the nitrous oxide comprises alternating anaerobic and anoxic stages in which phosphate is incorporated into cell biomass in the form of poly-phosphate.

12. The method of claim 11 further comprising recovering phosphorus from the cell biomass as poly-phosphate.

* * * * *